US009415094B2

(12) United States Patent
Meilhac

(10) Patent No.: US 9,415,094 B2
(45) Date of Patent: Aug. 16, 2016

(54) METHOD OF REDUCING SIDE EFFECTS ASSOCIATED WITH ADMINISTRATION OF TISSUE PLASMINOGEN ACTIVATOR (TPA)

(75) Inventor: Olivier Meilhac, Paris (FR)

(73) Assignee: INSERM (Institut National de la Sante et de la Recherche Medicale), Paris (FR)

( * ) Notice: Subject to any disclaimer, the term of this patent is extended or adjusted under 35 U.S.C. 154(b) by 1 day.

(21) Appl. No.: 13/349,905

(22) Filed: Jan. 13, 2012

(65) Prior Publication Data

US 2012/0177626 A1    Jul. 12, 2012

Related U.S. Application Data

(63) Continuation-in-part of application No. PCT/EP2010/060330, filed on Jul. 16, 2010.

(30) Foreign Application Priority Data

Jul. 16, 2009    (EP) .................................... 09305678

(51) Int. Cl.
    *A61K 38/57*    (2006.01)
    *A61K 9/127*    (2006.01)
(52) U.S. Cl.
    CPC .............. *A61K 38/57* (2013.01); *A61K 9/1275* (2013.01); *G01N 2800/2871* (2013.01)
(58) Field of Classification Search
    None
    See application file for complete search history.

(56) References Cited

U.S. PATENT DOCUMENTS

| 5,587,366 A | 12/1996 | Parker et al. |
| 2009/0110739 A1 | 4/2009 | Lacko et al. |

FOREIGN PATENT DOCUMENTS

| WO | 99/08701 | 2/1999 |
| WO | 01/56579 | 2/2001 |
| WO | 03/018047 | 3/2003 |
| WO | 03/097696 | 5/2003 |
| WO | 2006/100567 | 3/2006 |
| WO | 2008/068866 | 6/2008 |
| WO | 2009/025754 | 2/2009 |

OTHER PUBLICATIONS

Kilic E et al. (2001). Effects of Recombinant Tissue Plasminogen Activator After Intraluminal Thread Occlusion in Mice; Role of Hemodynamic Interactions. Stroke, v32, p. 2641-2647.*
Griffin JH et al. (1999). High-density lipoprotein enhancement of anticoagulant activities of plasma protein S and activated protein C. J. Clin. Invest., v103, p. 219-227.*
NINDS stroke study group (1995). Tissue Plasminogen Activator for Acute Ischemic Stroke. The New England Journal of Medicine, v333(24), p. 1581-1587.*
Cockerill GW et al. (2001). High density lipoproteins reduce organ injury and organ dysfunction in a rat model of hemorrhagic shock. FASEB J, v15, p. 1941-1952.*
Ortiz-Munoz G et al. (epub May 9, 2009). HDL antielastase activity prevents smooth muscle anoikis, a potential new antiatherogenic property. FASEB J, v23, p. 3129-3139.*
UMass Medical School (2002). HDL The Good Cholesterol, 1 page plus appended snapshot for publication date.*
Adan et al. (2009). Fish as diet resource in North Spain during the Upper Paleolithic. Journal of Archaeological Science, v36(3), p. 895-899.*
Zivin (Jul. 2009). Acute Stroke Therapy with Tissue Plasminogen Activator (tPA) since it was approved by the U.S. Food and Drug Administration (FDA), v66, p. 6-10.*
Paterno et al. (2004). Reconstituted High-Density Lipoprotein Exhibits Neuroprotection in Two Rat Models of Stroke. Cerebrovascular Diseases, v17, p. 204-211.*
Balaz et al. (2004). Uptake and transport of high-density lipoprotein (HDL) and HDL-associated a-tocopherol by an in vitro blood—brain barrier model. Journal of Neurochemistry, v89, p. 939-950.*
Wannamethee et al. (2000). HDL-Cholesterol, Total Cholesterol, and the Risk of Stroke in Middle-Aged British Men. Stroke, v31, p. 1882-1888.*
Lapergue et al. (epub Jun. 3, 2010). Protective Effect of High-Density Lipoprotein-Based Therapy in a Model of Embolic Stroke. Stroke, v41, p. 1536-1542.*
Abboud et al: "Alpha1-antitrypsin deficiency" Respiratory medicine, vol. 1 No. 3, pp. 80-87, 2006, XP024989323.
Aviram M: "Does paraoxonase play a role in susceptibility to cardiovascular disease?" Molecular medicine today, vol. 5 No. 9, pp. 381-386, 1999, XP002992784.
De Castro Ribeiro M et al: "Thrombin in ischemic neuronal death" Experimental neurology, vol. 198 No. 1, pp. 199-203, 2006, XP024945742.
Hacquebard M et al: "Changes in plasma LDL and HDL composition in patients undergoing cardiac surgery". Lipids, vol. 42 No. 12, pp. 1143-1153, 2007 XP007910059.
Kato Nobuyoshi et al: "Effects of trans-4-aminomethylcyclohexane carboxylic acid as an antifibrinolytic agent on arterial wall and experimental atherosclerotic lesions in rabbits". Thrombosis et diathesis haemorrhagica, vol. 24 No. 1, pp. 85-89, XP009139202.
Koudinov A R et al: "HDL Phospholipid: A natural inhibitor of Alzheimer's amyloid beta-fibrillogenesis?". Clinical Chemistry and laboratory medicine, vol. 37 No. 9, pp. 993/994, 1999, XP000996279.
Ortiz-Munoz G et al: "Alpha 1-Antitrypsin associated with HDL inhibits anoikis of vascular cells: a new anti-atherogenic property for HDL". Atherosclerosis supplements, vol. 9 No. 1, p. 2, 2008, XP022651508.
Rensen P C N et al: "Recombinant Lipoproteins : Lipoprotein-like lipid particles for drug targeting". Advanced drug delivery reviews, vol. 47 No. 2-3, pp. 251-276, 2001, XP002273271.

(Continued)

*Primary Examiner* — Scott Long
*Assistant Examiner* — Sean C Barron
(74) *Attorney, Agent, or Firm* — McAndrews Held and Malloy

(57) ABSTRACT

Provided is an HDL comprising an agent selected from the group consisting of antiproteases, antioxidants, antimitotics, anti-apoptotic agents and agents involved in the iron metabolism for use in methods of reducing side effects associated with administration of tissue plasminogen activator (tPA) in subjects in need of treatment.

13 Claims, 13 Drawing Sheets

(56) References Cited

OTHER PUBLICATIONS

Figure 1:
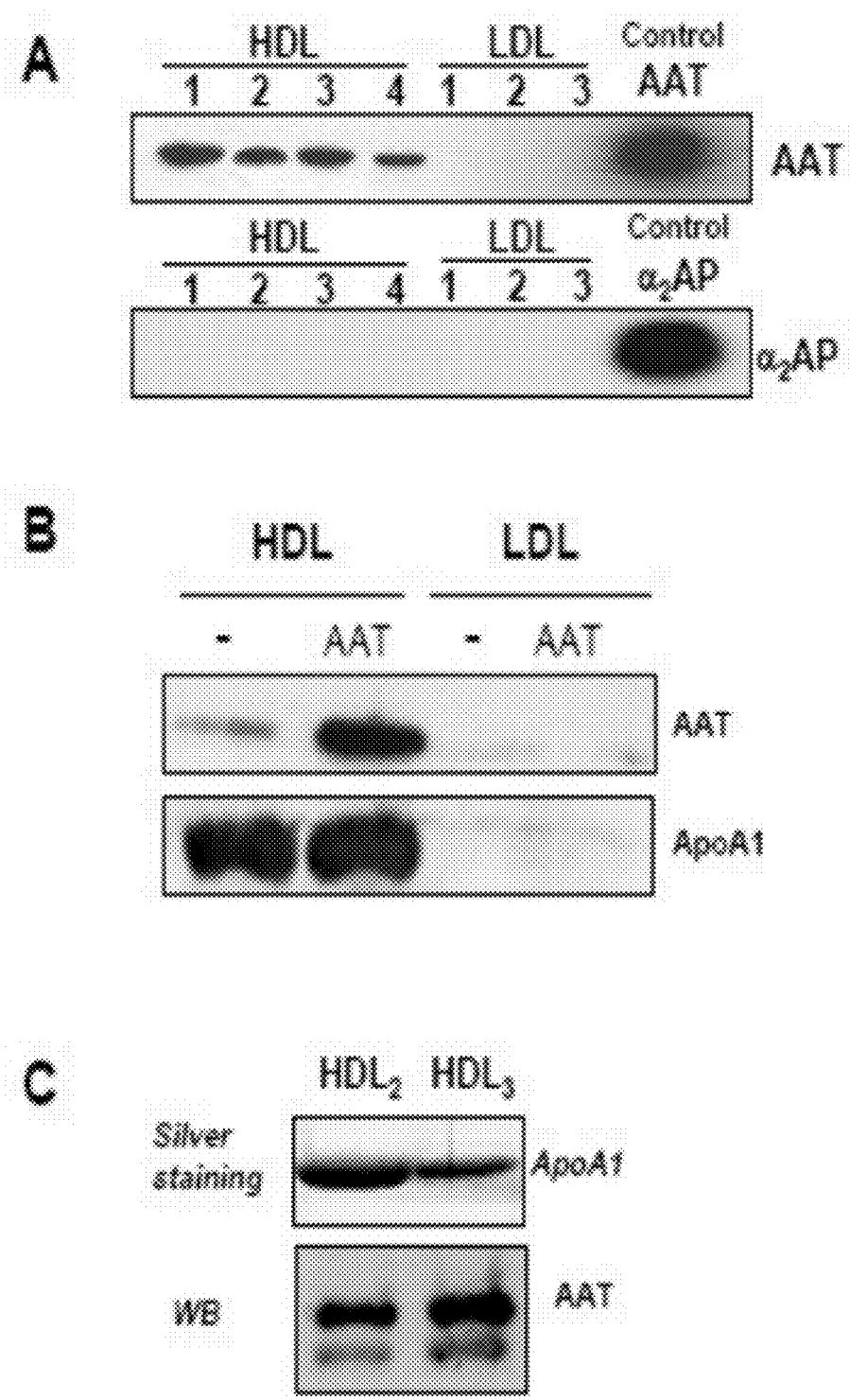

Schneeberger S et al: "Protease inhibitors as a potential target in modulation of postischemic inflammation". Drug news and perspectives, vol. 45 No. 9, pp. 568-574, 2002, XP009021572.

Sirtori C R et al: "High density Lipoprotein Administration : A new therapeutic modality for the treatment of cardiovascular diseases". Current medicinal chemistry. Immulogy, endocrine and metabolicagents, vol. 5, No. 4, 2005, XP008078020.

Vaisar Tomas et al: "Shotgun proteomics implicates protease inhibition and complement activation in the antiinflammatory properties of HDL". Journal of clinical investigation, vol. 17 No. 3, pp. 746-756, 2007, XP007911950.

Zuliani et al: "The anti-atherogenic properties of HDL particles". International congress series, excerpta medica, vol. 1303, 2007, pp. 103-110, XP022169313.

* cited by examiner

METHOD OF REDUCING SIDE EFFECTS ASSOCIATED WITH ADMINISTRATION OF TISSUE PLASMINOGEN ACTIVATOR (TPA)

The present application is filed as a continuation-in-part application of International Patent Application No. PCT/EP2010/060330, which was filed Jul. 16, 2010, claiming the benefit of priority to European Patent Application No. 09305678.6, which was filed on Jul. 16, 2009. The entire text of the aforementioned applications is incorporated herein by reference in its entirety.

FIELD OF THE INVENTION

The present disclosure provides native and recombined HDL for use in the treatment of a variety of conditions or diseases, including emphysema.

BACKGROUND OF THE INVENTION

High density lipoprotein (HDL) is one of the five major groups of lipoproteins (chylomicrons, VLDL, IDL, LDL, HDL) which enable lipids like cholesterol and triglycerides to be transported.

HDL is discoidal in shape with a core of non-polar lipids, triaglycerols and cholesterol esters, and a surface monolayer of phospholipids and non-esterified cholesterol. Several apolipoproteins reside in HDL. The major apolipoprotein is apolipoprotein A-I (Apo A-I), which is a 28-kDa single polypeptide consisting of 243 amino acid residues. (Jay H. Stein, Internal medicine, Edition 5, Elsevier Health Sciences, 1998; 2515 pages).

The protective role of high density lipoprotein (HDL) has been confirmed in a number of studies, and plasma levels of HDL and its major protein Apo A-I are consistently inversely correlated with atherothrombotic risk (B G Choi et al., *The role of high-density lipoprotein cholesterol in atherothrombosis*, Mt Sinai J Med. 2006 July; 73(4):690-701).

Alpha-1 antitrypsin (AAT) is a 52 kD glycoprotein. Its principal function is to inhibit neutrophil elastase, preventing tissue damage. AAT deficiency leads to obstructive pulmonary diseases and liver dysfunction. Currently the most widely used treatment is an intravenous infusion of highly purified human AAT. Intravenous augmentation therapy has been demonstrated to be safe and weekly infusions of AAT result in plasma AAT concentrations that are above those considered protective. (R C Hubbard et al., *Alpha-1 antitrypsin augmentation therapy for alpha-1 antitrypsin deficiency*, Am J Med. 1988 Jun. 24; 84(6A):52-62).

SUMMARY OF THE INVENTION

The inventors have shown that HDL can carry many agents other than apolipoprotein A-I. The inventors have also shown the presence of AAT in HDL and have demonstrated that HDL inhibit elastase activity and prevent its associated effects such as apoptosis.

Furthermore, the inventors have shown that HDL can be enriched in a therapeutic agent and be used as a vector able to reach specific organs.

The present invention provides an HDL comprising an agent for use as a medicament, wherein said agent is selected from the group consisting of antiproteases, antioxidants, antimitotics, agents involved in the iron metabolism and anti-apoptotic agents.

In one embodiment of the invention, the HDL according the invention is a native HDL.

In another embodiment of the invention, the HDL according the invention is a reconstituted HDL.

The invention provides an HDL comprising an antiprotease for use in the treatment of atherothrombosis, ischemic diseases, chronic obstructive pulmonary diseases, neurodegenerative diseases, cancer, in-stent restenosis, and all pathologies involving endothelial dysfunction.

The invention provides an HDL comprising an antioxidant for use in the treatment of atherothrombosis, ischemic diseases, chronic obstructive pulmonary diseases, neurodegenerative diseases, cancer, in-stent restenosis, and all pathologies involving endothelial dysfunction.

The invention provides an HDL comprising an antimitotic for use in the treatment of cancer and in-stent restenosis.

The invention provides an HDL comprising an agent involved in iron metabolism for use in the treatment of atherothrombosis, ischemic diseases, chronic obstructive pulmonary diseases and neurodegenerative diseases.

The invention provides an HDL comprising an anti-apoptotic agent for use in the treatment of atherothrombosis, ischemic diseases, chronic obstructive pulmonary diseases and all pathologies involving endothelial dysfunction.

The invention also relates to a method for protecting the blood brain barrier and alleviating the deleterious effect of injection of recombinant tissue plasminogen activator (rtPA), in a subject in need thereof, comprising the administration to said subject of an HDL. Preferably, said administration of an HDL is an injection.

DETAILED DESCRIPTION OF THE INVENTION

The present invention provides an HDL comprising an agent selected from the group consisting of antiproteases, antioxidants, antimitotics, agents involved in the iron metabolism and anti-apoptotic agents for use as a medicament.

HDL may represent a vector for proteins or peptides reported to be associated with HDL isolated from healthy subjects, because of their natural affinity for HDL particles (Karlsson H et al. *Lipoproteomics II: mapping of proteins in high-density lipoprotein using two-dimensional gel electrophoresis and mass spectrometry*, Proteomics. 2005; 5(5):1431-45; T Vaisar et al., *Shotgun proteomics implicates protease inhibition and complement activation in the anti-inflammatory properties of HDL*, J Clin Invest. 2007; 117(3): 746-56). In addition, in case of reconstituted HDL, purified Apo A-I is mixed with phospholipids such as phosphatidylcholines. During this particular step, proteins, peptides or other molecules that do not exhibit a natural affinity for HDL may be trapped within the nascent particles and forced to be carried by HDL (P C Rensen et al., *Recombinant lipoproteins: lipoprotein-like lipid particles for drug targeting*, Adv Drug Deliv Rev. 2001 Apr. 25; 47(2-3):251-76).

As used herein, the term "HDL" encompasses native HDL or reconstituted HDL.

Typically, the agent comprised in the HDL according the invention has either lipophilic properties or an affinity for some proteins constituting the HDL. Alternatively, the agent may be chemically modified to improve its association with HDL.

In one embodiment of the invention, the HDL is a native HDL.

As used herein, the term "native HDL" refers to HDL purified from human healthy donors. Typically, HDL can be isolated by two different methods: ultracentrifugation and immunosorption. Isolation of HDL by immunosorption is performed using anti-Apo A-I column prepared by crosslinking goat polyclonal antibodies directed against Apo A-I to Sepharose beads. Isolation of HDL by ultracentrifugation is performed by classical double-step ultracentrifugation in KBr density gradient interval of 1.063-1.210 g/ml. It falls within the ability of the skilled man to carry out such methods.

In another embodiment of the invention, the HDL is a reconstituted HDL.

As used herein, the terms "reconstituted HDL", "rHDL" or "synthetic HDL" refer to a particle structurally analogous to native HDL, composed of a lipid or lipids in association with at least one of the proteins of HDL, preferably Apo A-I, and which exhibits all of the known physiological functions of HDL. Typically, the components of reconstituted HDL may be derived from blood, or produced by recombinant technology.

Typically, reconstituted HDL may be prepared by complexation of Apo A-I to phospholipids. Methods for obtaining reconstituted HDL are disclosed in EP 1 425 031 and U.S. Pat. No. 5,652,339.

Typically, suitable lipids for the preparation of rHDL are phospholipids, preferably phosphatidylcholine, for example 1-palmitoyl-2-linoleoyl phosphatidylcholine (PC) or 1,2-dipalmitoyl PC. Optionally, rHDL contains other lipids, for example cholesterol, cholesterol esters, triglycerides, or other lipids. The lipids may be synthetic, naturally occurring lipids or combinations thereof.

Typically, native HDL or reconstituted HDL have a molar ratio of phospholipid/Apo A-I from 2 to 250, preferably from 10 to 200, more preferably from 20 to 100, more preferably 20 to 50 and most preferably from 30 to 40.

Further, rHDL may optionally contain additional lipids such as cholesterol, cholesterol esters, triglycerides and/or sphingolipids, preferably in a molar ratio of lipid/Apo A-I up to 20.

Typically, the HDL according to the invention can be administered by injection and/or, e.g. by intra-arterial, intra-peritoneal or preferably intravenous injection in a dosage which is sufficient to obtain the desired pharmacological effect.

Typically, the loading of HDL according to the invention with an agent selected from the group consisting of antiproteases, antioxidants, antimitotics, agents involved in the iron metabolism, and anti-apoptotic agents may be performed as follows:
   incubation of HDL with said agent at an appropriate concentration under gentle agitation at 37° C. for an appropriate time, said concentration and time depending on the affinity of the agent for the HDL; then
   ultracentrifugation after adjustment of the density, overlay with KBr solution and finally saline solution; and
   HDL enriched with said agent are collected and either dialyzed against saline solution or filtered using a centrifugal device.

Alternatively, the loading of HDL according to the invention with an agent selected from the group consisting of antiproteases, antioxidants, antimitotics, agents involved in the iron metabolism, and anti-apoptotic agents may be performed as follows:
   incubation of HDL with said agent is performed under gentle agitation at 37° C. for an appropriate time; and
   filtration using a cut-off centrifugal device. Free agent goes in the flow-through whereas enriched HDL remain in the upper compartment.

The person skilled in the art would be aware of the conditions for carrying out said loading. For example, if the agent has a low affinity with the HDL, the HDL will be incubated with a higher concentration of said agent and for a longer time, than if the agent had a natural and high affinity for the HDL.

In addition, the person skilled in the art is able to select the appropriate Molecular Weight Cutoff of the centrifugal device for carrying out the above mentioned filtrations.

Typically, native HDL may be loaded with agents which are naturally present in the composition of the native HDL so that to increase by 5 to 20 times their natural content in said agents. Such a loading noticeably improves the efficiency of the HDL in the treatment of various diseases as disclosed hereafter.

Alternatively, native HDL may be loaded with agents which are not naturally present in the composition. Such a loading provides new properties to the HDL of the invention, which are thus useful in the treatment of various diseases as disclosed hereafter.

Typically, the HDL according to the invention can be administrated by intra-arterial injection during a thrombectomy procedure performed for reperfusion during acute stroke. Endovascular therapy has become a promising alternative for patients who are ineligible for or have failed intravenous (IV) thrombolysis. (R G Nogueira, et al., *Endovascular approaches to acute stroke, part 2: a comprehensive review of studies and trials*, AJNR Am J Neuroradiol. 2009 May; 30(5):859-75 & M Mazighi, et al., *Comparison of intravenous alteplase with a combined intravenous-endovascular approach in patients with stroke and confirmed arterial occlusion (RECANALISE study): a prospective cohort study*, Lancet Neurol, 2009 September; 8(9):802-9). The HDL according to the present invention can also be administrated through an aerosol.

HDL Comprising an Antiprotease

The invention relates to an HDL comprising an antiprotease.

Typically, said antiprotease is selected from the group consisting of:
   alpha-1 antitrypsin, (SERPINA1 serpin peptidase inhibitor, clade A-IPI00305457, AAT), which is an elastase inhibitor;
   elafin (PI3: Peptidase Inhibitor 3), which is an inhibitor of elastase;
   protease-nexin 1, which is an inhibitor of thrombin, plasmin and plasminogen activators;
   alpha-2-anti-plasmin (IPI00029863), which is a plasmin inhibitor;
   monocyte/neutrophil elastase inhibitor (MNEI, SERPINB1), which is an inhibitor of elastase, proteinase 3 and cathepsin G;
   inter-alpha-trypsin inhibitor (IPI00218192);
   tissue-inhibitors of Matrix Metalloproteinases; and
   alpha-1 antichymotrypsin.

In one embodiment of the invention, the molar ratio antiprotease/Apo A-I is at least 0.1, preferably from 0.1 to 200, preferably from 0.1 to 100, more preferably from 1 to 50 and most preferably from 10 to 50.

In a particular embodiment, native HDL are enriched with antiproteases such as to increase by 5 to 20 times their natural content in said antiproteases.

Determination of the Apo A-I and antiprotease levels falls within the ability of the person skilled in the art. Typically, said levels can be assessed by commercially available ELISAs. Alternatively, and for qualitative results, both Apo A-I and AAT can be evaluated by Western blotting, using a known quantity of both proteins to make a standard curve after densitometric quantification. The presence of peptides and proteins with antiprotease activities after HDL enrichment may also be monitored by mass spectrometry.

In one embodiment of the invention, the HDL comprising an antiprotease is used in the treatment chronic obstructive pulmonary diseases, especially emphysema.

It is well established that AAT is useful in the treatment of emphysema.

Emphysema is defined on an anatomical basis as a disease characterized by structural changes in the lung causing increase, beyond the normal range, in the size of air spaces distal to terminal bronchioles. The inventors have shown that the clinical manifestations of the disease is preventable by augmenting AAT levels in the lung by administering HDL or HDL enriched in alpha-1 antitrypsin. Alpha-1 antitrypsin is useful in the protection against proteolytic damage of alveoli in the lung, in particular by neutrophil elastase activity.

The inventors have shown that it is possible to enrich human isolated HDL with purified AAT increasing by 5 to 20 times their natural content in AAT. Normal concentrations of AAT range from 1 to 3 g/L, of which less than 1% is carried by circulating HDL.

Preferably, the molar ratio of antiprotease/Apo A-I in an HDL according to the invention loaded with antiproteases is from 1 to 200, preferably from 2 to 100, most preferably from 10 to 50.

Hence, the loading of HDL with alpha-1 antitrypsin provides higher concentrations of AAT and improves the efficiency of said HDL in the treatment of chronic obstructive pulmonary diseases, especially emphysema.

Typically, the loading of HDL with AAT may be performed as follows:
- incubation of HDL at 1 mg/mL with AAT under gentle agitation at 37° C. for 2 hours; then
- ultracentrifugation after adjustment of the appropriate density (1.25 for native HDL) and overlay with KBr solution and finally saline solution; and
- HDL enriched with AAT are collected and either dialyzed against saline solution or filtered using a 5 kDa cut-off centrifugal device.

Alternatively, the loading of HDL may be performed as follows:
- incubation of HDL at 1 mg/mL with AAT under gentle agitation at 37° C. for 2 hours; and
- filtration using a 100 kDa cut-off centrifugal device. Free AAT goes in the flow-through, whereas enriched HDL remain in the upper compartment.

In another embodiment of the invention, the HDL comprising an antiprotease is used in the treatment of ischemic diseases, especially stroke, transient ischemic accident and myocardial infarction.

The inventors have shown and exemplified that HDL comprising antiproteases are useful in the treatment of ischemic diseases, especially stroke.

In still another embodiment of the invention, the HDL comprising an antiprotease is used in the treatment of neurodegenerative disorders.

It is well known that antiproteases are useful in the treatment of neurodegenerative disorders (S. Eriksson et al., *Alpha 1-antichymotrypsin regulates Alzheimer beta-amyloid peptide fibril formation*, Proc. Natl. Acad. Sci. Vol 92, pp 2313-2317, 1995).

In yet another embodiment of the invention, the HDL comprising an antiprotease is used in the treatment of atherothrombosis, especially coronary, carotid and peripheral artery disease and abdominal aortic aneurysm.

The inventors have shown and exemplified that AAT associated with HDL is decreased in the case of atherothrombosis, in which elastase activity is increased. Thus, HDL comprising an antiprotease is useful in the treatment of atherothrombosis.

In a further embodiment of the invention, the HDL comprising an antiprotease is used in the treatment of cancer. It is well known that antiproteases are useful in the treatment of cancer. (Li W et al., *Matrix metalloproteinase-26 is associated with estrogen-dependent malignancies and targets alpha-1 antitrypsin serpin* Cancer Res. 2004 Dec. 1; 64(23): 8657-65; Uetsuji S et al, *Effect of aprotinin on metastasis of Lewis lung tumor in mice*, Surg Today. 1992; 22(5):439-42). Recent studies report that elastase is able to degrade intracellular substrates leading to increased tumor growth (A M Houghton et al., *Neutrophil elastase-mediated degradation of IRS-1 accelerates lung tumor growth*, Nat Med. 2010 February; 16(2):219-23). The inventors have shown that HDL and HDL enriched with antiproteases are able to be taken up by different cell types including smooth muscle cells and endothelial cells, and vectorize antiproteases within the cells.

In a further embodiment of the invention, the HDL comprising an antiprotease is used in the treatment of in-stent restenosis.

Antiprotease are useful in the treatment of in-stent restenosis (Andrade-Gordon P et al., *Administration of a potent antagonist of protease-activated receptor-1 (PAR-1) attenuates vascular restenosis following balloon angioplasty in rats*, J Pharmacol Exp Ther. 2001 July; 298(1):34-42).

In still another embodiment, the HDL comprising an antiprotease is used in the treatment of pathologies involving endothelial dysfunction, such as sepsis or ischemia/reperfusion conditions including myocardial infarction and stroke. The inventors have indeed shown and exemplified that native and reconstituted HDL provide a protective effect on the blood brain barrier (BBB).

The invention further relates to a method for treating a subject suffering from atherothrombosis, ischemic diseases, chronic obstructive pulmonary diseases, neurodegenerative diseases, cancer, in-stent restenosis, or all pathologies involving endothelial dysfunction comprising the step of administering an effective amount of an HDL comprising an antiprotease to said object.

By an "effective amount of an HDL" is meant a sufficient amount to treat a subject, at a reasonable benefit/risk ratio applicable to any medical treatment. It will be understood, however, that the total daily usage of HDL will be decided by attending physician within the scope of sound medical judgment. The specific therapeutically effective dose level for any particular subject in need thereof will depend upon a variety of factors including the stage of the disease or disorder being treated and the activity of the specific HDL, the age, body weight, general health, sex and diet of the subject, the time of administration, route of administration, the duration of the treatment, drugs used in combination or coincidental with the treatment.

HDL Comprising an Antioxidant

The invention relates to an HDL comprising an antioxidant. Typically, said antioxidant is selected from the group consisting of:
- Paraoxonase 1, 2 or 3, paraoxonase 1, 2 or 3 inhibits intracellular oxidative stress and allows the detoxification of organo-phosphorus compounds;
- Catalase, catalase participates in $H_2O_2$ detoxification;
- Vitamin E, Vitamin E is a lipophilic antioxidant;
- Omega-3 fatty acids, such as eicosapentaenoic acid, EPA (C20:5) and docosahexaenoic acid, DHA (C22:6);
- Butylated Hydroxytoluene;
- N-acetyl cystein;

Polyphenols, such as resveratrol and hydroxytyrosol which inhibit lipoprotein oxidation;

Thioredoxins, a family of antioxidant enzymes preventing the development of emphysema;

Estrogens, reported to protect the endothelium via its antioxidant activity. For instance, estradiol potentiates endothelial nitric oxide and prostacyclin production; and Others molecules able to bind the estrogen receptor alpha such as polyphenols contained in the red wine, that display antioxidant and anti-atherogenic properties.

In one embodiment of the invention, the molar ratio antioxidant/Apo A-I is at least 0.1, preferably from 0.1 to 200, preferably from 0.1 to 100, more preferably from 1 to 50 and most preferably from 10 to 50.

In a particular embodiment, native HDL are enriched with antioxidants such as to increase by 5 to 20 times their natural content in said antioxidants.

Determination of the Apo A-I and antioxidant levels falls within the ability of the person skilled in the art.

Typically, the level of Apo A-I can be assessed by commercially available ELISAs. If the antioxidant is a protein, its level can be assessed by commercially available ELISAs. If the antioxidant is a lipid or another type of molecule, its level can be assessed by mass spectrometry. Alternatively, if the antioxidant is a protein, both Apo A-I and antioxidant can be evaluated by Western blotting, using a known quantity of both proteins to make a standard curve after densitometric quantification.

In one embodiment of the invention, the HDL comprising an antioxidant is used in the treatment of atherothrombosis, especially coronary, carotid and peripheral artery disease and abdominal aortic aneurysm and in the treatment of ischemic diseases, especially stroke, transient ischemic accident and myocardial infarction.

It is well known that oxidative stress participates in proatherogenic mechanisms of vascular dysfunction and atherothrombosis (Z S Nedeljkovic et al., *Mechanisms of oxidative stress and vascular dysfunction*, Postgraduate Medical Journal 2003; 79:195-200). Furthermore, the antioxidants have cardioprotective effects. (N. Dhalla, A Elmoselhi, T Hata and N Makino, *Status of myocardial antioxidants in ischemia-reperfusion injury*, Cardiovascular Research 2000, 47(3):446-456). Thus, antioxidants by suppressing oxidative stress are useful in the treatment of atherothrombosis and ischemic diseases.

In another embodiment of the invention, the HDL comprising an antioxidant is used in the treatment of chronic obstructive pulmonary diseases, especially emphysema.

It is well established that antioxidants are also useful in the treatment of chronic obstructive pulmonary diseases, especially for the treatment of emphysema (A Cantin et al., *Oxidants, antioxidants and the pathogenesis of emphysema*, Eur J Respir Dis Suppl., 1985; 139:7-17).

In a further embodiment of the invention, the HDL comprising an antioxidant is used in the treatment of neurodegenerative diseases.

It is well known that antioxidants are useful in the treatment of neurodegenerative disorders (B Moosmann et al., *Antioxidants as treatment for neurodegenerative disorders*, Expert Opinion on Investigational Drugs, October 2002, vol. 11, No. 10, pages 1407-1435).

In yet another embodiment of the invention, the HDL comprising an antioxidant is used in the treatment of cancer and in-stent restenosis.

It is well established that antioxidants are useful in the treatment of cancer (Bardia A. et al, *Anti-inflammatory drugs, antioxidants, and prostate cancer prevention*, Curr Opin Pharmacol. 2009 Jun. 30). It also well known that antioxidants are useful in the treatment of in-stent restenosis (J E Schneider et al., *Probucol decreases neointimal formation in a swine model of coronary artery balloon injury: A possible role for antioxidants in restenosis*, Circulation, Vol 88, 628-637).

In still another embodiment, the HDL comprising an antioxidant is used in the treatment of pathologies involving endothelial dysfunction, such as sepsis or ischemia/reperfusion conditions including myocardial infarction and stroke.

The inventors have indeed shown and exemplified that native HDL provide a protective effect on the blood brain barrier (BBB).

The invention further relates to a method for treating a subject suffering from atherothrombosis, ischemic diseases, chronic obstructive pulmonary diseases, neurodegenerative diseases, cancer, in-stent restenosis, or all pathologies involving endothelial dysfunction, comprising the step of administering an effective amount of an HDL comprising an antioxidant to said subject.

HDL Comprising an Antimitotic

The invention relates to an HDL comprising an antimitotic.

Typically, said antimitotic is Siromilus, also named Rapamycin.

In one embodiment of the invention, the molar ratio antimitotic/Apo A-I is at least 0.1, preferably from 0.1 to 200, preferably from 0.1 to 100, more preferably from 1 to 50 and most preferably from 10 to 50.

In a particular embodiment, the native HDL are enriched with antimitotics such as to increase by 5 to 20 times their natural content in said antimitotics.

Determination of the Apo A-I and antimitotic levels falls within the ability of the person skilled in the art. Typically, said levels can be assessed by commercially available ELISAs. Alternatively, and for qualitative results, said levels can be evaluated by Western blotting, using a known quantity of both proteins to make a standard curve after densitometric quantification. The enrichment by small molecules should be evaluated by specific methods such as mass spectrometry.

In one embodiment of the invention, the HDL comprising an antimitotic is used in the treatment of cancer and in-stent restenosis.

Protein kinases have emerged as a key regulator of all aspects of neoplasia, including proliferation, invasion, angiogenesis and metastasis. Rapamycin (Siromilus) and its derivatives inhibit the downstream kinase mammalian target of rapamycin (mTOR). mTOR inhibitors potently suppress growth and proliferation of lymphocytes and certain tumour cell lines. Thus, Siromilus is useful in the treatment of cancer. (J Dancey et al., *Issues and progress with protein kinase inhibitors for cancer treatment*, Nature Publishing Group, volume 2, April 2003, 293-313).

In addition of its antiproliferative property, Siromilus possess an antimigratory property. Siromilus provides protection against intimal hyperplasia after stent implantation in coronary arteries and, potentially, in peripheral arteries. Thus, Siromilus is useful for reducing the incidence of restenosis. (S Marx et al., *The Development of Rapamycin and Its Application to Stent Restenosis*; Circulation, 2001; 104:852).

The invention further relates to a method for treating a subject suffering from cancer or in stent restenosis comprising the step of administering an effective amount of an HDL comprising an antimitotic to said subject.

HDL Comprising an Agent Involved in the Iron Metabolism

The invention relates to an HDL comprising an agent involved in the iron metabolism.

Typically, said agent involved in the iron metabolism is selected from the group consisting of:

Transferrin, which is involved in the iron uptake by macrophage;

Haptoglobin, which is involved in the hemoglobin uptake by macrophages; and

Hepcidin, which is involved in the iron metabolism.

In one embodiment of the invention, the molar ratio agent involved in the iron metabolism/Apo A-I is at least 0.1, preferably from 0.1 to 200, preferably from 0.1 to 100, more preferably from 1 to 50 and most preferably from 10 to 50.

In a particular embodiment, native HDL are enriched with agents involved in the iron metabolism such as to increase by 5 to 20 times their natural content in said agents.

Determination of the level of Apo A-I and the level of the agent involved in the iron metabolism falls within the ability of the person skilled in the art. Typically, said levels can be assessed by commercially available ELISAs. Alternatively, and for qualitative results, said levels can be evaluated by Western blotting, using a known quantity of both proteins to make a standard curve after densitometric quantification. The enrichment by small molecules should be evaluated by specific methods such as mass spectrometry.

In one embodiment, the HDL comprising an agent involved in iron metabolism is used in the treatment of atherothrombosis, especially coronary, carotid and peripheral artery disease, and abdominal aortic aneurysm.

It is well known that intraplaque haemorrhage is a factor of vulnerability of atherothrombotic plaques. This includes the release of haemoglobin and associated heme containing the prooxidant iron. Thus, agents involved in the iron metabolism are useful in the treatment of atherothrombosis (R. T. Calado et al., *HFE gene mutations in coronary atherothrombotic disease*, Braz J Med Biol Res. 2000 March; 33(3):301-6).

In another embodiment, the HDL comprising an agent involved in iron metabolism is used in the treatment of ischemic diseases, especially stroke, transient ischemic accident, and myocardial infarction.

It is well known that transferrin has a protective role in acute stroke (C Altamura et al, *Ceruloplasmin/Transferrin system is related to clinical status in acute stroke*, Stroke. 2009 April; 40(4):1282-8. Epub 2009 Feb. 19). Thus, agents involved in iron metabolism are useful in the treatment of ischemic diseases.

In still another embodiment, the HDL comprising an agent involved in iron metabolism is used in the treatment of chronic obstructive pulmonary diseases, especially emphysema.

In a further embodiment, the HDL comprising an agent involved in iron metabolism is used in the treatment of neurodegenerative diseases.

It has been established that iron metabolism is involved in neurodegenerative disorders, such as Parkinson's disease and as Alzheimer's disease (D Gerlach et al., *Altered Brain Metabolism of Iron as a Cause of Neurodegenerative Diseases?*, Volume 63 Issue 3, pages 793-807). Hence, agents involved in iron metabolism are useful in the treatment of neurodegenerative diseases.

The invention further relates to a method for treating a subject suffering from atherothrombosis, ischemic diseases, chronic obstructive pulmonary diseases or neurodegenerative diseases comprising the step of administering an effective amount of an HDL comprising an agent involved in iron metabolism to said subject.

HDL Comprising an Anti Apoptotic Agent

The invention relates to an HDL comprising an anti-apoptotic agent.

Typically, said anti-apoptotic agent is selected from the group consisting of:

Sphingosine-1-phosphate (S1P), which is a bioactive lipid generated in the intracellular membranes from the metabolism of sphingomyelin, reported to be anti-apoptotic (Morales A, Fernandez-Checa J C *Pharmacological modulation of sphingolipids and role in disease and cancer cell biology*. Mini Rev Med Chem. 2007. 7(4): 371-82);

Paraoxonase 1 and 2;

Catalase;

Omega-3 fatty acids, including Docosahexaenoic acid (DHA; 22:6n-3), an omega-3 essential fatty acid family member, precursor of neuroprotectin D1, which downregulates apoptosis and, in turn, promotes cell survival. (Belayev L et al. *Robust docosahexaenoic acid-mediated neuroprotection in a rat model of transient, focal cerebral ischemia*. Stroke. 2009; 40(9):3121-6);

Resolvin E1 (RvE1), an anti-inflammatory mediator derived from eicosapentaenoic acid (Keyes K T et al. *Resolvin E1 protects the rat heart against reperfusion injury*. Am J Physiol Heart Circ Physiol. 2010; 299(1): H153-64); and Clusterin or apolipoprotein J, naturally present in HDL (Djeu J Y, Wei S. *Clusterin and chemoresistance* Adv Cancer Res. 2009; 105:77-92).

Preferably, said anti-apoptotic agent is S1P. HDL-associated S1P is responsible for the beneficial effects of HDL on vasorelaxation, cell survival, cell adhesiveness, angiogenesis and synthesis of two powerful endogenous anti-atherogenic and anti-thrombotic molecules such as nitric oxide (NO) and prostacyclin (PGI2) (C Rodriguez et al. *Sphingosine-1-phosphate: A bioactive lipid that confers high-density lipoprotein with vasculoprotection mediated by nitric oxide and prostacyclin*. Thromb Haemost. 2009 April; 101(4):665-73).

In one embodiment of the invention, the molar ratio anti-apoptotic agent/Apo A-I is at least 0.1, preferably from 0.1 to 400, preferably from 0.1 to 200, more preferably from 1 to 100 and most preferably from 10 to 50.

Determination of the level of Apo A-I and the level of the anti-apoptotic agent falls within the ability of the person skilled in the art.

Typically, the level of Apo A-I can be assessed by commercially available ELISAs. If the anti-apoptotic agent is a protein, its level can be assessed by commercially available ELISAs. If the anti-apoptotic agent is a lipid or another small molecule, its level can be assessed by mass spectrometry. Alternatively, if the anti-apoptotic agent is a protein, both Apo A-I and anti-apoptotic agent can be evaluated by Western blotting, using a known quantity of both proteins to make a standard curve after densitometric quantification.

In a particular embodiment, native HDL are enriched with anti-apoptotic agents naturally present in the composition of native HDL so as to increase by 5 to 20 times their natural content in said agents.

In another embodiment, native HDL are enriched with anti-apoptotic agents not naturally present in the composition of native HDL so as to increase by 10 to 200 times the molar ratio anti-apoptotic agent/Apo A-I.

In one embodiment, the HDL comprising an anti-apoptotic agent is used in the treatment of atherothrombosis, ischemic diseases, chronic obstructive pulmonary diseases and all pathologies involving endothelial dysfunction.

The invention further relates to a method for treating a subject suffering from atherothrombosis, ischemic diseases, chronic obstructive pulmonary diseases or all pathologies involving endothelial dysfunction comprising the step of administering an effective amount of an HDL comprising an anti-apoptotic agent to said subject.

The invention also relates to a method for alleviating the deleterious effect of an injection of tissue plasminogen activator (preferably recombinant tPA), in a subject in need thereof, comprising the administration to said subject of an HDL according to the invention. Said HDL according to the invention is an HDL comprising an agent selected from the group consisting of antiproteases, antioxidants, antimitotics, agents involved in the iron metabolism and anti-apoptotic agents.

Preferably, said administration of an HDL is an injection. Preferably, the subject in need thereof is a subject suffering from stroke.

Preferably, the method aims to reduce the risk of hemorrhagic complications due to an injection of tissue plasminogen activator in a subject in need thereof, and comprises the administration to said subject of an HDL according to the invention. Indeed, as shown in example 8, the injection of an HDL according to the invention protects the BBB and reduces the incidence of hemorrhage induced by tPA.

In the following, the invention will be illustrated by means of the following examples as well as the figures.

FIGURES LEGENDS

FIG. 1: HDL isolated by ultracentrifugation contains alpha-1 antitrypsin.

(A) HDL and LDL from human plasma were isolated by two-step ultracentrifugation on KBr gradient density. Four different batches of lipoproteins (5 µg) were immunoblotted with alpha-1 antitrypsin (AAT, 200 ng) and alpha-2-antiplasmin ($\alpha_2$AP, 100 ng) antibodies. HDL contained AAT but no $\alpha_2$AP.

(B) One hundred µg of HDL and LDL were incubated overnight (16 h) with 100 µg AAT in a total volume of 200 µL at 37° C. under gentle shaking. Both lipoproteins were then isolated by ultracentrifugation and 1 µg of each were loaded for Western Blot analysis against AAT and Apo A-I. Results are representative of 3 independent experiments.

(C) $HDL_2$ and $HDL_3$ fractions isolated by ultracentrifugation were either silver stained (top panel) or submitted to Western blot analysis using an anti-AAT antibody (bottom panel). Gels shown are representative of 4 independent experiments.

Figure 2:
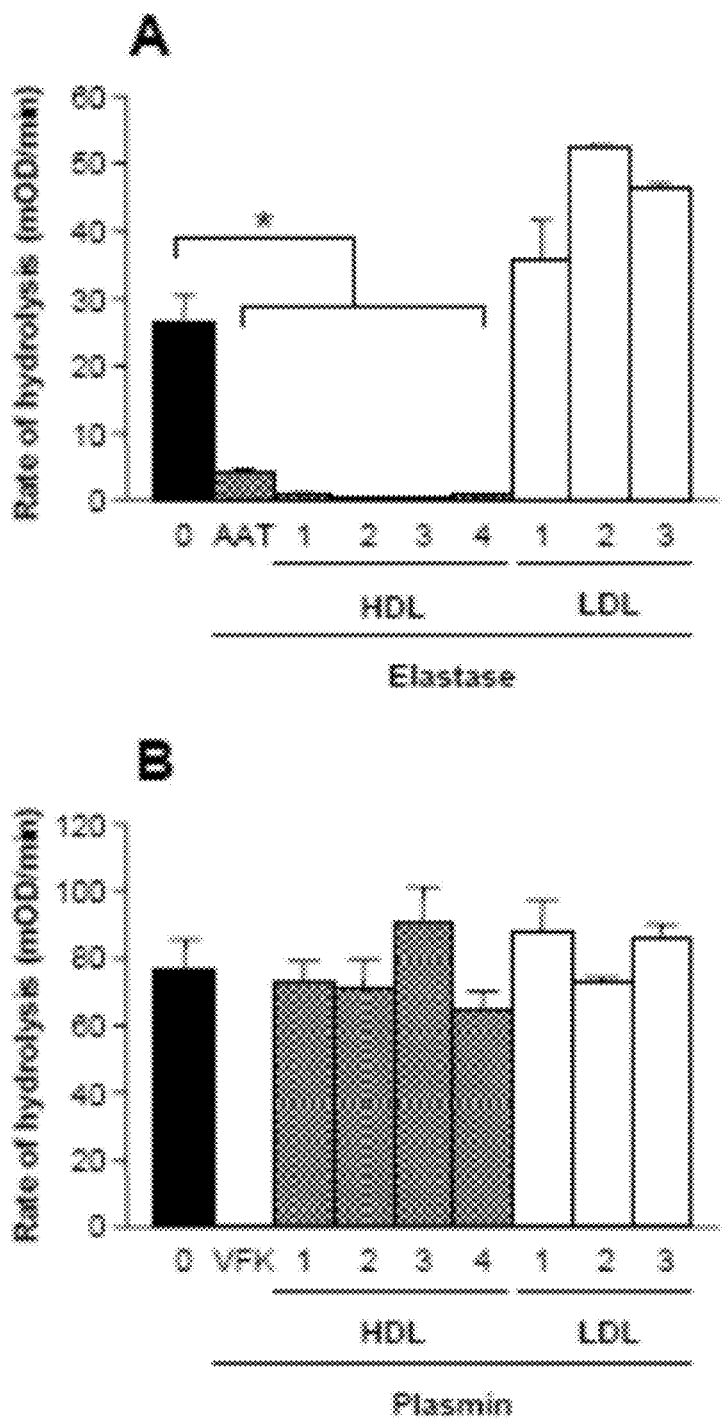

FIG. 2: HDL but not LDL exhibits anti-elastase activity. (A) Leukocyte elastase (10 nM) was incubated with a chromogenic substrate (MeO-Suc-Ala-Ala-Pro-Val-pNa) in the presence or not of 50 µg/mL HDL (4 different batches) or LDL (3 different batches). AAT (10 nM) was used as a positive control of elastase inhibition. Data of rate of hydrolysis (mOD/min) are mean±SD of 4 experiments performed in triplicate (*, P<0.01 vs elastase alone). (B) Plasmin activity is not affected by incubation with HDL or LDL (50 µg/mL). Val-Phe-Lys peptide (VFK) was used as plasmin inhibitor.

Figure 3:
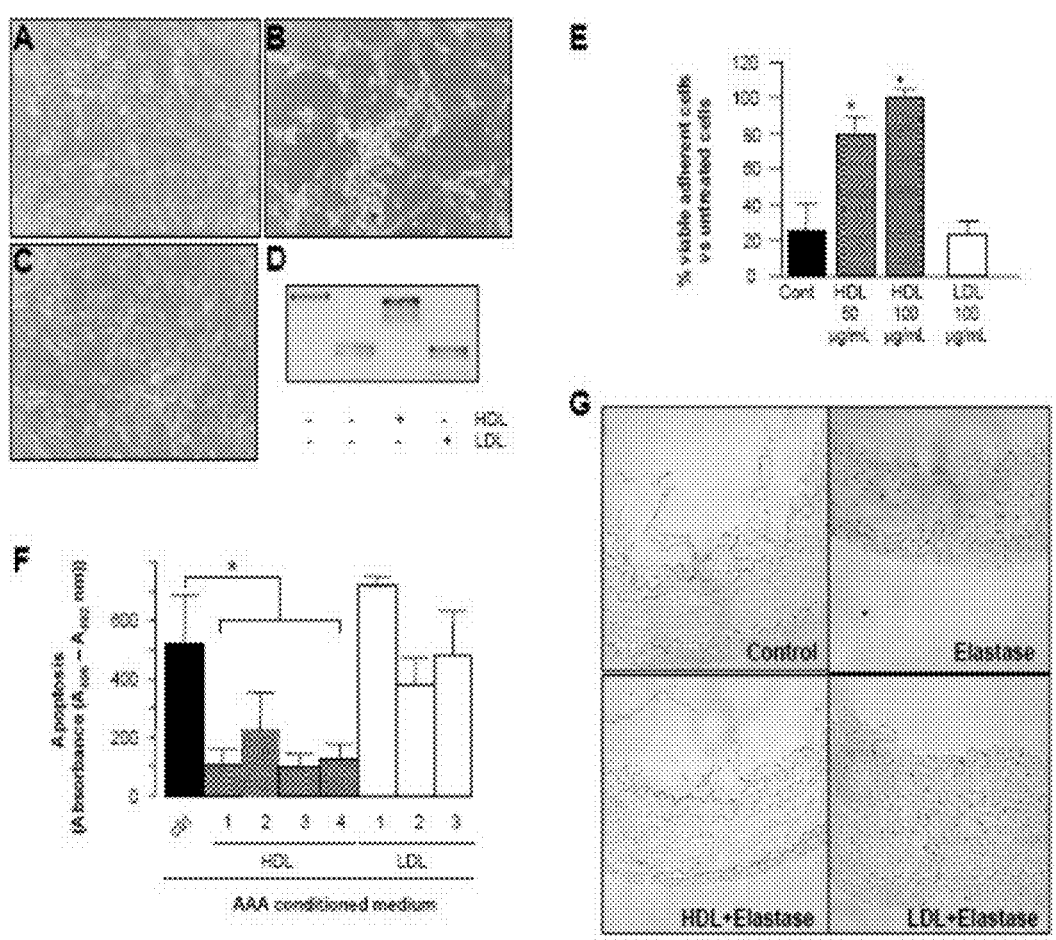

FIG. 3: HDL inhibit anoikis induced by leukocyte elastase. (A-C) photomicrographs of human VSMCs in culture. (A) Untreated control cells. (B) VSMCs treated by elastase (10 nM) alone for 16 hours, or (C) in the presence of 50 µg/mL HDL. (D) Incubation with HDL prevents fibronectin degradation by leukocyte elastase. Representative Western blot detecting fibronectin in the cell culture supernatant. (E) Viable adherent VSMCs were quantified by using the MTT test after treatment by elastase (10 nM). Results are expressed as percentages of untreated control cells. Each column represents the mean±SD of 4 separate experiments performed in triplicate (*, P≤0.005 vs elastase). (F) Quantification of apoptosis in cells incubated with medium conditioned by the luminal layer of AAA intraluminal thrombus for 24 hours in the presence or absence of 100 µg/mL HDL or LDL from 4 and 3 different subjects, respectively. Results are expressed as percentages of untreated cells (ctrl absorbance: 0.082±0.028 nm). Each column represents the mean±SD of 2 separate experiments performed in duplicate with media conditioned by AAA intraluminal thrombus from 5 different patients (*, P<0.05 vs treatment without HDL). (G) Detection of apoptotic nuclei by Apostain® (positive nuclei appear in brown) after incubation of human mammary endarteries with 10 nM elastase ±50 µg/mL HDL or LDL for 24 hours.

Figure 4:
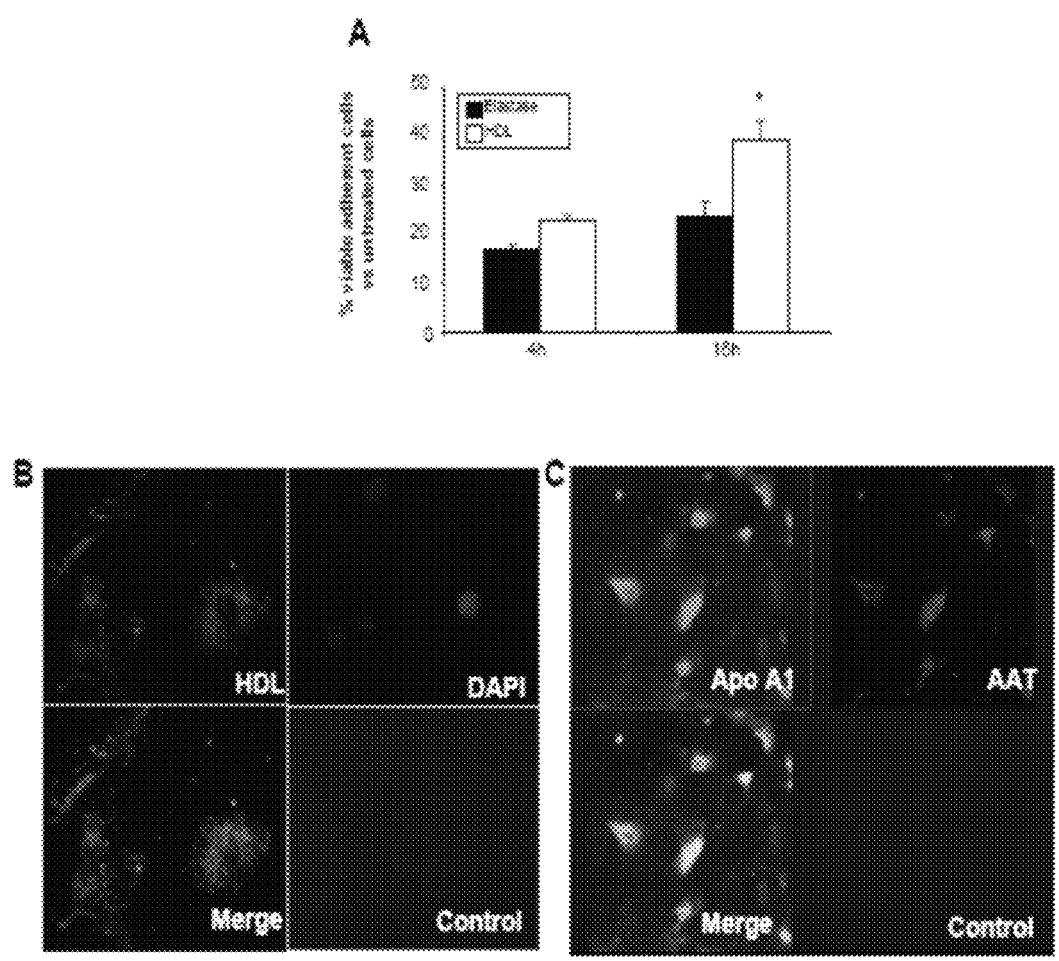

FIG. 4: Intracellular HDL prevents elastase-induced apoptosis. (A) MTT test. 100 µg/mL of HDL were pre-incubated for 4 and 16 h and then the cells were rinsed before incubation with 10 nM elastase for 16 hours. Values are means±SD (*p<0.005 versus elastase alone). (B) 100 µg/mL of HDL HDL labelled with DI-C18 carbocyanines were incubated for 8 hours with VSMCs, counterstained with DAPI and observed under an epifluorescence microscope. (C) Double immunostaining was performed for apo-AI and AAT after incubation with 50 µg/mL HDL for 4 hours. Observations were made by confocal microscopy (apo-AI—green, AAT-red, colocalization in yellow).

Figure 5:
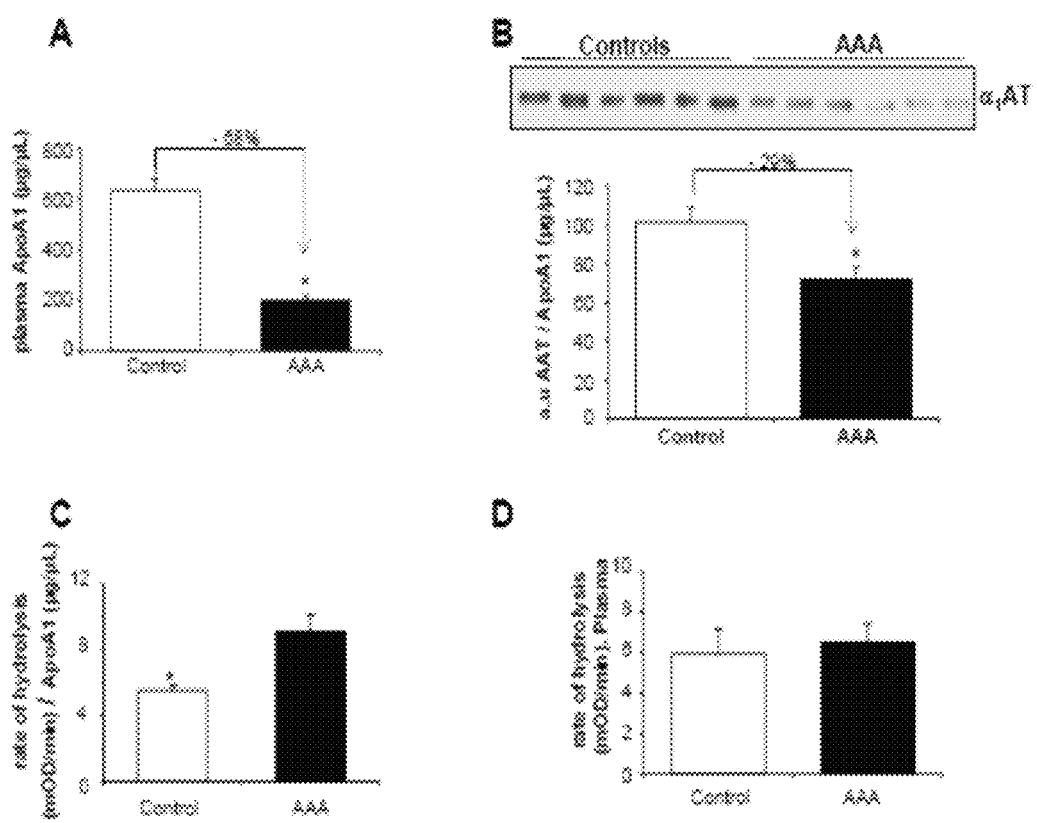

FIG. 5: Patients with AAA carry less $\alpha_1$AT associated with elastase activity. (A) Apo A-I levels measured by ELISA are significantly decreased in plasma of patients with AAA (n=13) relative to control subjects (n=23). Data are means±SD (*, P<0.0001 vs healthy controls). (B) HDLs isolated individually from each subject were immunoblotted for detection of AAT. Values obtained by densitometric analysis of the bands were normalized to HDL-Apo A-I concentration. Representative Western blot showing 6 patients and 6 control HDL (out of a total of 43 samples analyzed, results are expressed in arbitrary units/µg/µL Apo A-IµL*, p<0.0001 vs. control). (C) Leukocyte elastase (10 nM) was incubated with HDLs in order to assess their anti-elastase activity. Results are expressed in (mOD/min)/µg/µL apo-A1. Elastase inhibitory potential is significantly reduced in HDL from patients with AAA (*, P<0.0001 vs. control group). (D) Plasma anti-elastase activity was tested in vitro by incubating leukocyte elastase with diluted plasma (1:1000) from healthy controls and AAA patients. Results are expressed in mOD/min.

Figure 6:
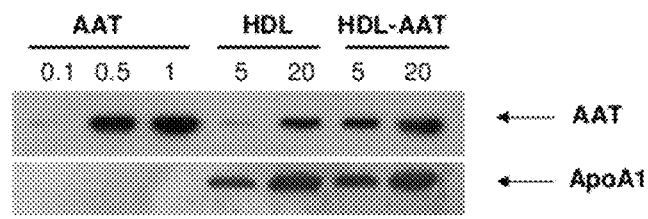

FIG. 6: Western Blot detection of AAT and apolipoprotein A-I. Different amounts of AAT were loaded in a SDS-polyacrylamide gel (0.1 to 1 µg) as well as 5 or 20 µg HDL. After migration under reducing conditions, the gel was transblotted to a nitrocellulose membrane and a classical procedure of Western Blot was used with anti-AAT and anti Apo AI antibodies).

Figure 7:
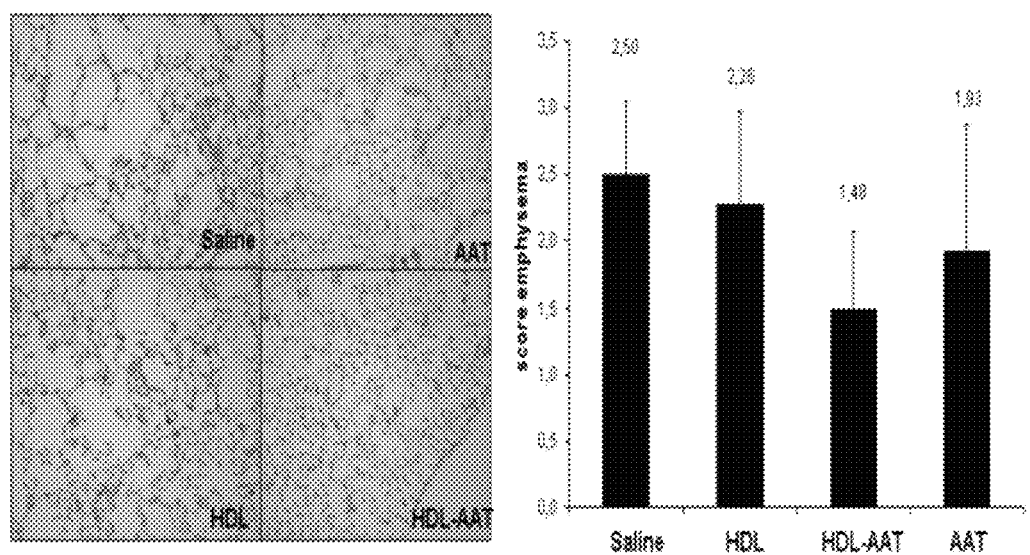

FIG. 7: Hematoxylin/eosin staining on great-axis sagittal sections (5 µm) of the left lung, from mice instillated with elastase and then injected 4 times with saline, AAT (3.5 mg/kg), HDL or HDL-AAT (75 mg/kg) during the first week (left). Semi-quantification of emphysema development (right).

Figure 8:
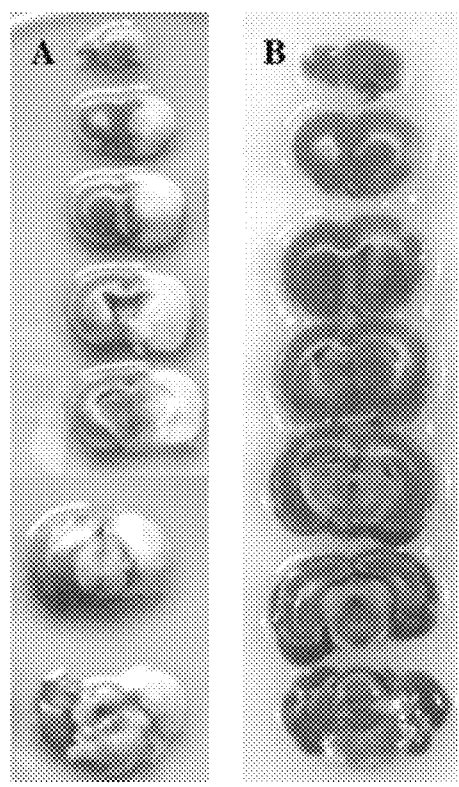

FIG. 8: Effect of HDL therapy in the acute phase of stroke. Cerebral infarct measurement using TTC staining 24 hours after stroke onset. The infarct appears white on a background of red normal brain. Figure A: rat treated by vehicle. Figure B: Rat treated by HDL infusion (10 mgKg) after stroke onset.

Figure 9:
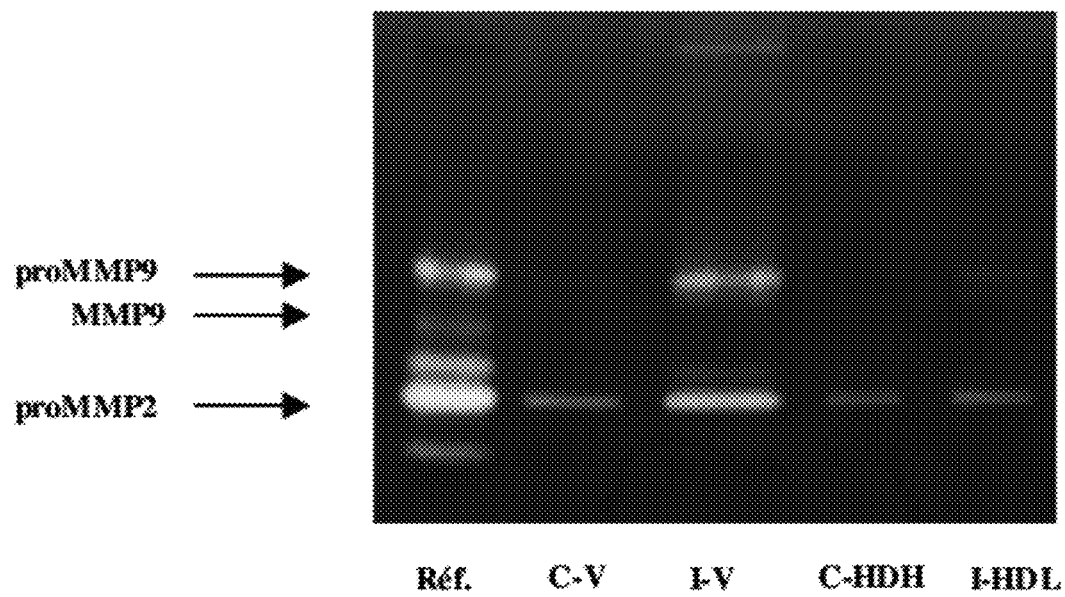

FIG. 9: Representative gelatin zymograms. ProMMP9/MMP9 and MMP2 activities are increased in infarct area (I) versus non infarct area (C) at 24 hours after stroke onset. HDL infusion is associated with a marked decrease in proMMP9/MMP9 activation in infarct area.

Ref.: reference containing proMMP2/9 and active MMP2/9.

C-V: controlateral hemisphere to ischemia from vehicle group.

I-V: Infarct area from vehicle group.

C-HDLV: controlateral hemisphere to ischemia from HDL group.

I-HDL: Infarct area from HDL group.

Figure 10:
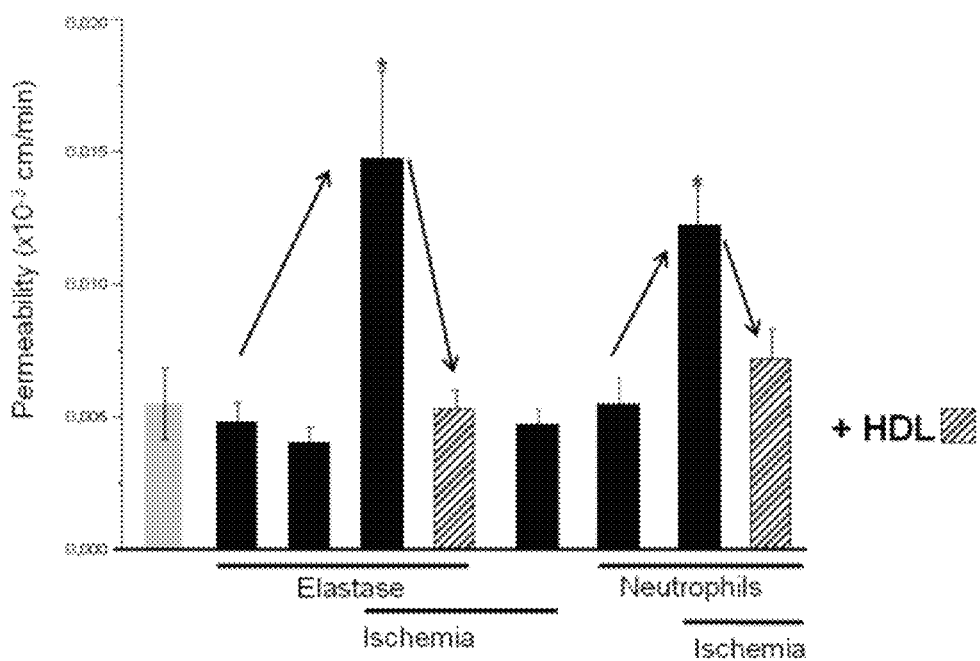

FIG. 10: Effects of elastase and of neutrophils on permeability of blood brain barrier (BBB) under normal or ischemic conditions.

Purified elastase and neutrophils induced an increase of BBB permeability only under ischemic conditions. HDL (purified from human plasma) were able to inhibit significantly this protease-mediated increase in BBB permeability.

Figure 11:
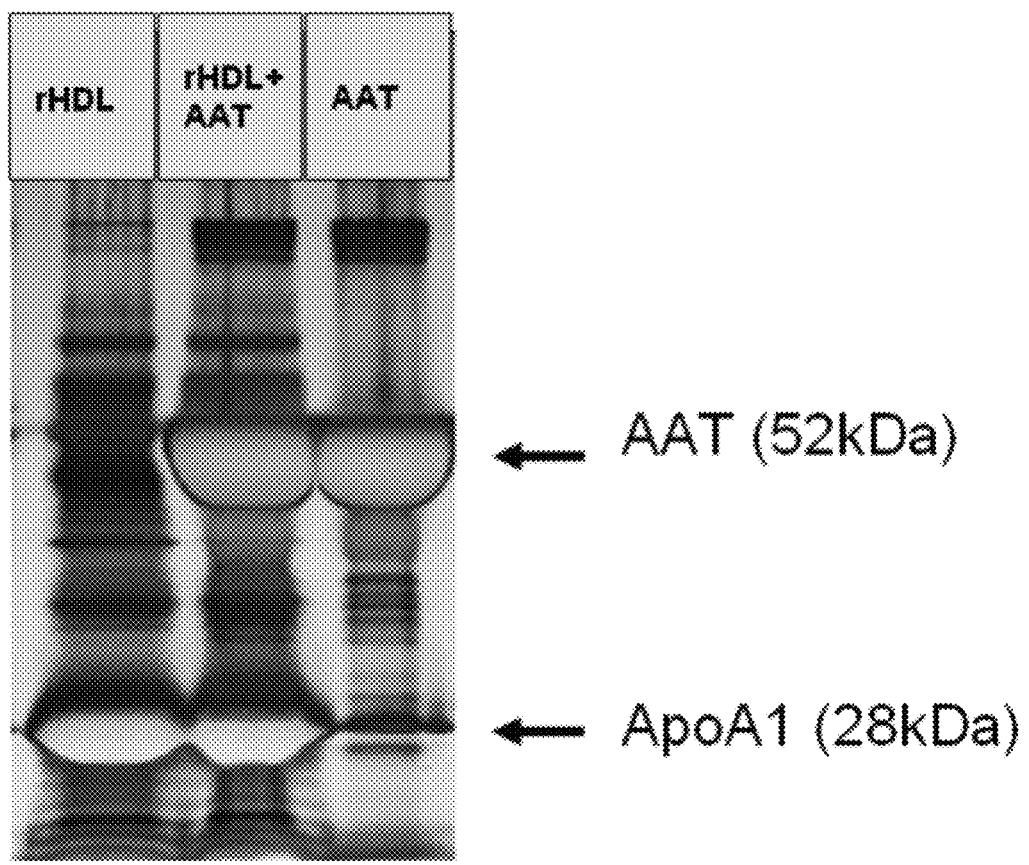

FIG. 11: Silver nitrate staining after SDS-PAGE showing enrichment of HDL with AAT.

Figure 12:
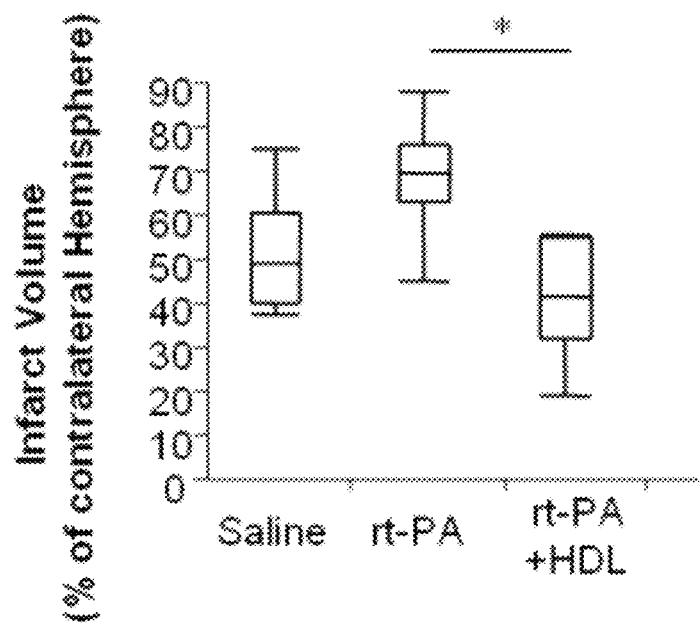
Figure 12:
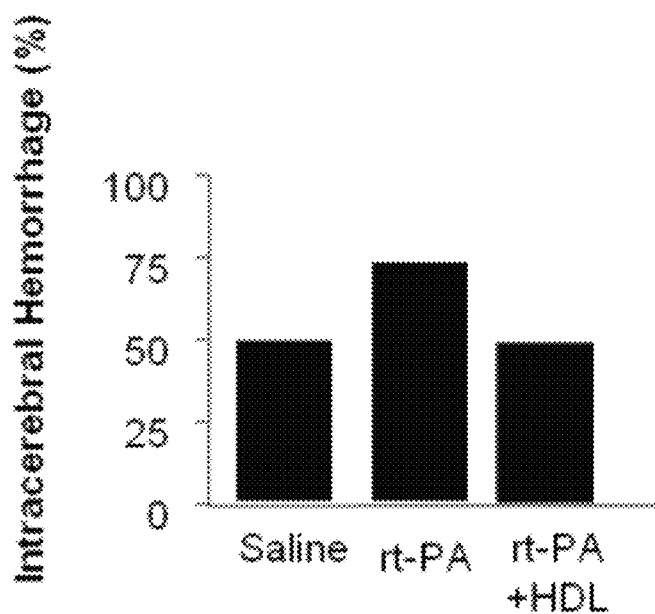

FIG. 12: Protective effect of intravenous injection of HDL after treatment with recombinant tissue plasminogen activator (rtPA) in rats suffering from stroke.

A: Measure of the infract volume (% contralateral hemisphere) in rat treated with saline administration, recombinant tissue plasminogen activator (rtPA), and rtPA along with HDL.

B: Macroscopic evaluation of the the presence of hemorrhage in rat treated with saline administration, recombinant tissue plasminogen activator (rtPA), and rtPA along with HDL.

Figure 13:
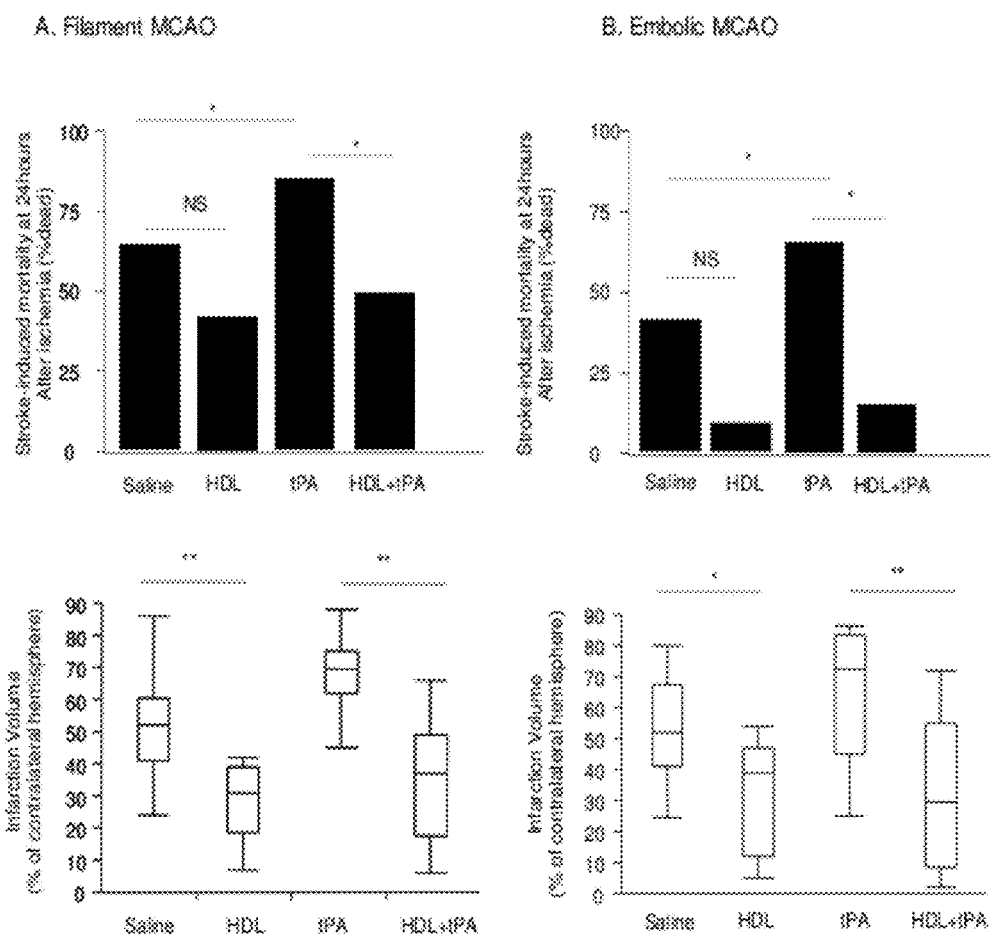

FIG. 13. Effect of HDL and tPA on mortality and infarct volume in focal stroke models (A. transient filament MCO, fMCAO; B. embolic MCAO, eMCAO).

A: tPA increased mortality rate compared to three other groups (*$P<0.05\%$). HDL decreased significantly stroke-induced mortality in HDL+tPA-treated group compared to tPA alone in both models.

B: HDL decreased significantly infarct volume at 24 hours after stroke versus saline and in combination with tPA versus tPA alone (n=12/group). *$P≤0.05$. **$P≤0.001$.

Figure 14:
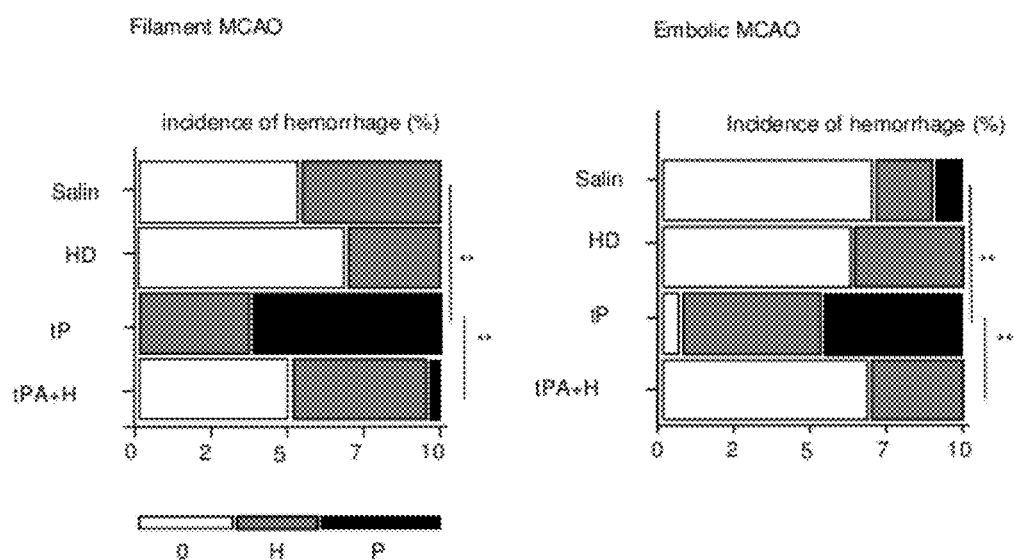

FIG. 14. Effect of HDL and tPA on intracerebral hemorrhage in focal stroke models Parenchymal hematoma were significantly increased in tPA-treated groups versus saline groups in both models ($P≤0.001$). Combined treatment with HDL (10 mg/kg) dramatically prevented parenchymal hematoma ($P≤0.001$, n=12/group).

Figure 15:
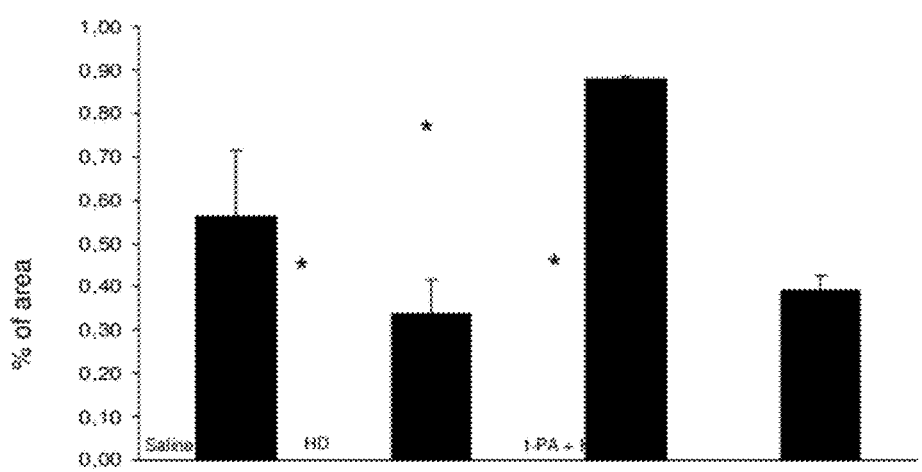

FIG. 15. Effect of HDL and tPA on brain edema and IgG extravasation. tPA significantly increased IgG extravasation in the ischemic hemisphere versus saline. Combined treatment with HDL significantly prevented this increase (*$P<0.05$, n=3/groups).

Figure 16:
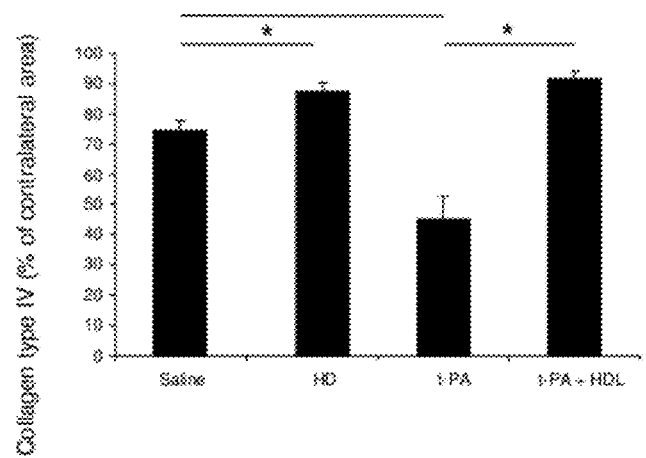

FIG. 16. Assessment of blood brain barrier injury by collagen IV immunoreactivity in cerebral microvessels. Quantification of collagen IV immunoreactivity vessels in ischemic area (*$P<0.05\%$, n=4/group).

Figure 17:
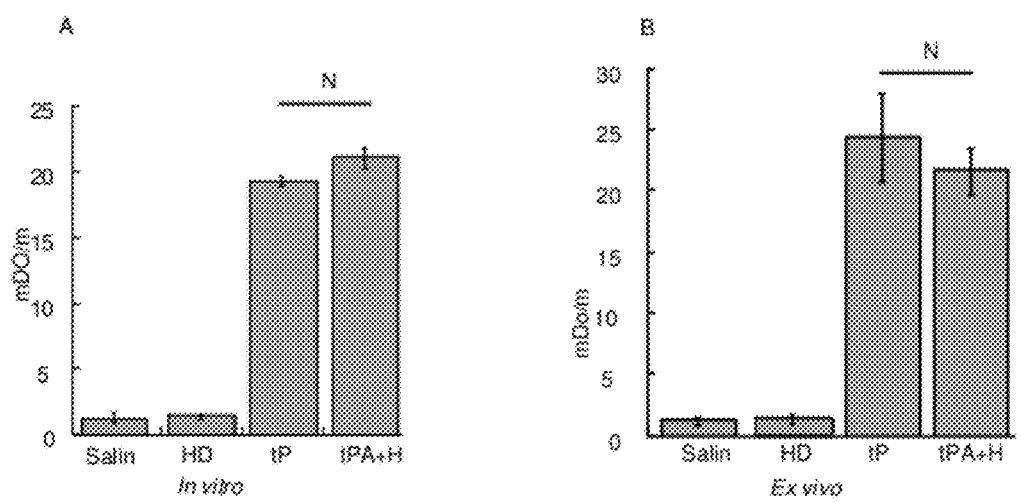

FIG. 17. Impact of HDL on proteolytic activity of tPA.

A: In vitro, HDL do not affect the proteolytic action of tPA.

B: Ex vivo study on collected plasma from rat treated with HDL, tPA, or both. Combination therapy with HDL and tPA does not affect the proteolytic activity of tPA. (n=4/groups).

EXAMPLES

Example 1

HDL Anti-Elastase Activity Prevents Smooth Muscle Cell Anoikis, a New Anti-Atherogenic Property Various studies using proteomic approaches have shown that HDL can carry many proteins other than its constitutive apolipoprotein A-I. Using mass spectrometry and Western blot, the inventors have shown the presence of alpha-1 antitrypsin (SERPINA1 serpin peptidase inhibitor, clade A "AAT", an elastase inhibitor) in HDL, isolated either by ultracentrifugation or by selected-affinity immunosorption using an anti-apoA-I column. Furthermore, the inventors report that HDL possesses potent anti-elastase activity. The inventors have also shown that only HDL, and not LDL, is able to bind AAT. HDL-associated AAT was able to inhibit extracellular matrix degradation, cell detachment and apoptosis induced by elastase, in human vascular smooth muscle cells (VSMCs) and in mammary artery cultured ex-vivo. Degradation of fibronectin by elastase used as a marker of pericellular proteolysis was prevented by addition of HDL. Elastase present in aortic abdominal aneurysm (AAA) thrombus samples was also able to induce apoptosis of VSMCs in culture. This phenomenon was prevented by addition of HDL but not of LDL. Finally, the inventors report that the proportion of AAT in HDL isolated from patients with AAA is decreased relative to that from matched controls, indicating a reduced capacity of HDL to inhibit elastase in these patients. In conclusion, the inventors provide evidence of a new potential anti-atherogenic property of HDL attributable to AAT and its anti-elastase activity.

Plasma levels of HDL-cholesterol and its major protein apo A-I are consistently inversely correlated with atherothrombotic risk in observational studies. Beneficial effects of HDL are principally attributed to reverse transport of cholesterol, even though other anti-atherogenic properties are well documented, such as anti-oxidant, anti-inflammatory or anti-thrombotic effects. Several studies using proteomic approaches on HDL from healthy subjects have identified alpha-1 antitrypsin in $HDL_2$ and $HDL_3$ fractions. This serine protease inhibitor is the natural circulating inhibitor of neutrophil elastase. The inventors have shown that this protease is present in atherothrombotic lesions and circulating leukocyte elastase-alpha-1 antitrypsin complexes were correlated with carotid stenosis and a risk of myocardial infarction and stroke. In addition, the inventors have shown that neutrophil elastase present in the intraluminal thrombus of abdominal aortic aneurysm plays a pivotal role in the disappearance of arterial wall smooth muscle cells and subsequent absence of healing. Among the proteases reported to be present in the pathological arterial wall and able to induce apoptosis subsequent to extracellular matrix degradation, elastase is one of the most potent. Polymorphonuclear neutrophils (PMN) represent the main class of circulating leukocytes which are activated when they are trapped during the formation of the thrombus either in abdominal aortic aneurysm or in intraplaque hemorrhages, recently described as a driving force of atherosclerotic plaque evolution towards rupture. PMN degranulation leads to the release of elastase in the extracellular compartment, which is able to degrade many proteins of the extracellular matrix (ECM) such as elastin, fibronectin, thrombospondin, vitronectin etc. Proteolysis of the extracellular matrix destabilizes directly the arterial wall both directly by reducing its mechanical resistance and indirectly by inducing vascular cell apoptosis subsequent to rupture of cell-ECM contacts which normally convey survival signals. In the present study, the inventor have shown that alpha-1 antitrypsin (SERPINA1 serpin peptidase inhibitor, clade A "AAT"), the naturally occurring elastase inhibitor, is associated with HDL, and t that HDL thereby inhibit elastase activity and its deleterious effects in situ, such as ECM degradation and smooth muscle cell anoikis. In a second part, the inventors assessed the levels of HDL and AAT-HDL in the plasma of patients with or without AAA. Therefore, the inventors describe here a new function of HDL that could account for its anti-atherogenic potential, an anti-elastase activity possibly favoring arterial wall stabilization.

Materials and Methods

Reactives and Cell Culture

Human neutrophil elastase and alpha-1 antitrypsin were from Calbiochem. Human aortic vascular smooth muscle cells (VSMCs from Promocell) were cultured in medium (Promocell SM2) containing 10% fetal calf serum.

Isolation of Lipoproteins

Lipoproteins were isolated from healthy volunteers plasma sampled on EDTA by two different methods: ultracentrifugation and selected-affinity immunosorption. Isolation of HDL by immunosorption was performed. Briefly, an anti-Apo A-I column was prepared by crosslinking rabbit polycolonal antibodies directed against Apo A-I to Sepharose beads. A mock column without antibodies and an IgG column were prepared in the same conditions using non-relevant immunoglobulin G (Innovative research). Plasma from healthy subjects (non-smokers >50 years-old, with informed consent) was incubated overnight at 4° C. with Apo A-I, mock or IgG sepharose beads (1 mL of EDTA-plasma for 12.5 mL beads) under gentle shaking. The columns were then rinsed thrice with 5 volumes of saline (0.9% NaCl, 1 mM EDTA, 0.025% NaN3) containing additional NaCl to reach a 0.5M concentration. After a final wash with saline, the column was eluted with a solution containing 0.2M acetic acid, 0.15M NaCl pH3 and immediately buffered with Tris base to pH 7.9. HDL was then extensively rinsed with saline-EDTA and concentrated using a centrifugal concentrating device (cut-off 5 kDa, Vivascience). Alternatively, plasma density was adjusted to d=1.063 with KBr and overlaid with KBr saline solution (d=1.063). Ultracentrifugation was performed at 100,000 g for 20 hours at 10° C. The upper lipoprotein fraction containing LDL was adjusted to a density of 1.25 g/mL with KBr and then overlaid with saline (d=1.006) before ultracentrifugation at 100,000 g for 20 hours at 10° C. After this step, the LDL fraction (orange layer) was recovered as a single band and the KBr was eliminated by 3 washing steps using a centrifugal filter device. The density of the bottom fraction resulting from the first ultracentrifugation and containing HDL was adjusted to 1.25 g/mL with KBr and overlaid with saline/KBr solution (d=1.21). The second ultracentrifugation and subsequent washing steps are similar to those of LDL, except that HDL fractions represent the top layer of the tube. When indicated, $HDL_2$ and $HDL_3$ were collected separately. All fractions were desalted either by dialysis against saline or by centrifugation and 3 washes with saline.

2D Non-Denaturing Electrophoresis

Lipoproteins containing Apo A-I (LpAI) were purified from normolipidemic human plasma by anti-AI immunosorption column chromatography. Residual serum albumin and immunoglobulins were removed by passage over anti-HSA and Protein A sepharose columns. The LpAI fraction was analyzed by two-dimensional, agarose×PAG nondenaturing electrophoresis. LpAI was electrophoresed in 0.8% agarose (w/v) (Bio-Rad, Cat. #162-0126) prepared in 0.062 M tris, 0.027 M tricine, 0.005 M calcium lactate (pH 8.3) at a 15 V/cm field strength. The agarose strip was electrophoresed in a second dimension linear gradient of PAG (0-30% T) to equilibrium (3000 V-h) at 5° C. A mixture of proteins was used to calibrate (Stoke's diameter) the second dimension PAG and included: ovalbumin (6.0 nm), bovine serum albumin (7.1 nm), lactate dehydrogenase (8.1 nm), catalase (10.4 nm), ferritin (12.2 nm), thyroglobulin (17.0 nm), low density lipoprotein (d=1.030-1.050 g/ml, 25 nm).

Mass Spectrometry Analysis of HDL Species Separated by 2DN Gels

Proteins resolved by 2D PAG were prepared for mass spectrometry by in gel digestion with trypsin (Promega Cat. #V5111). Peptides were separated by reverse phase chromatography using an Ultimate HPLC system (Dionex). A C18 Pepmap100 column (75 um ID×15 cm) was employed with a gradient from 2 to 30% Acetonitrile/0.1% Formic acid over 38 minutes followed by increasing to 50% acetonitrile/0.1% formic Acid over a further two minutes. Eluting peptides were introduced into an LTQ-Orbitrap (Thermo) where data-dependent acquisition was used to fragment the six most abundant components observed in each survey scan, employing dynamic exclusion of previously fragmented components. Raw data was converted to peaklists using the Mascot Distiller v2.1.1.0, then analyzed using Protein Prospector v5.0 (http://prospector2.ucsf.edu) against the human entries of a database that consisted of the Uniprot database downloaded on $4^{th}$ December 2007, with a sequence shuffled/randomized decoy version concatenated onto the end of the database giving a total of 152244 entries searched. The concatenated database allowed for estimation of a peptide false positive rate. Search parameters required tryptic cleavage specificity with up to one missed cleavage, precursor mass accuracy of within 20 ppm and fragment mass accuracy of within 0.6 Da. Cysteine carbamidomethylation was searched for as a constant modification and methionine oxidation, pyroglutamate formation from peptide N-terminal glutamines and protein N-terminal acetylation were allowed for as variable modifications. Acceptance criteria were a minimum peptide score of 15, minimum protein score of 22 and a maximum expectation value of 0.1. For all spots analyzed there were a total of 1998 peptides reported above these thresholds, which included three matches to the decoy part of the database. Hence, the peptide false positive rate of identification for the dataset is around 0.3% ((3×2)/1998).

Western Blots on 2DN Gels

For immunoblots, calibrator proteins were biotinylated (Bio-Rad, Cat. #170-6529). Resolved proteins were electrophoretically transfered (55V, 18 h, 10° C.) onto nitrocellulose membranes (0.2 µm, Bio-Rad, Cat. #162-0212). Nonspecific binding was blocked with casein (25 mg/ml, 0.02 M tris, pH 8.5). Membranes were probed with antibodies to Apo A-I (custom produced goat polyclonal) and to alpha-1 antitrypsin (Calbiochem, mouse monoclonal Cat. #178260) and bound antibodies disclosed using biotinylated second antibodies, avidin-biotin-horseradish peroxidase conjugates (Pierce Chemical Co, Cat. #1852410), and 3,3'-diaminobenzidine (0.05%, w/v)/nickel chloride (2.5 mM)/H2O2 (0.05%, v/v) in 0.10 M imidazole (pH 7.0).

Western Blot Analysis Following SDS-PAGE

HDL and LDL (5 µg) from 4 and 3 different preparations, respectively, were resolved by SDS-12% PAGE. After electrophoresis, proteins were transferred onto nitrocellulose membranes, blocked with 5% milk powder in TBS-T (tris buffer saline, pH 7.4, 0.1% Tween20), and then probed with either rabbit polyclonal anti-alpha-2-antiplasmin (α2AP) (dilution 1:1000, Calbiochem) or rabbit polyclonal anti-AAT (dilution 1:1000, Dako) and peroxidase-conjugated secondary antibody (dilution 1:2500, Jackson Immunoresearch laboratories). Purified AAT (200 ng, Calbiochem) and α2AP (100 ng, Calbiochem) were used as controls.

For detection of fibronectin fragments in cell culture supernatant, 5 µL of conditioned medium were analyzed by SDS-8% PAGE. The transblotted membranes were then probed with a rabbit polyclonal anti-human fibronectin (dilution 1:1000 from Sigma).

In all cases, appropriate peroxidase-conjugated secondary antibody was used (dilution 1:2500, Jackson Immunoresearch laboratories) followed by ECL detection. Densitometry analysis was performed using a calibrated scanner (GS800 Bio-Rad).

Determination of Elastase and Plasmin Activities

Human neutrophil elastase (10 nM, Calbiochem) was incubated with 1.5 mM of an elastase chromogenic substrate, MeO-Suc-Ala-Ala-Pro-Val-pNa (Calbiochem) in PBS (100-μl final volume). Plasmin (10 nM, American Diagnostica) was incubated with 0.75 mM of the selective plasmin chromogenic substrate, CBS0065 (Diagnostica Stago, Asnières, France) in 50 mM phosphate buffer pH 7.4, 80 mM NaCl (100-μl final volume). AAT (40 nM), d-valyl-1-phenylalanyl-1-lysine chloromethylketone (10 μM, VFK, Calbiochem), a selective irreversible inhibitor of plasmin, HDL (50 μg or 1 to 4.5 μg for dose-response experiments) and LDL (50 μg) were pre-incubated with elastase or plasmin for 15 min at room temperature before the addition of the substrate. Human plasma (1:1000 dilution) or HDL from patients (1:4 dilution) were incubated in presence of 10 nM elastase in the same conditions. Substrate hydrolysis was monitored for 2 hours at 37° C. by spectrophotometry at 405 nm and 490 nm. HDL anti-elastase activity was normalized to HDL-Apo A-I quantity.

Cell Detachment Assay and Apoptosis

Human VSMCs were grown to confluence in 12-well plates and serum-deprived for 24 hours before stimulation. VSMCs were then incubated for 16 hours with 10 nM elastase (Calbiochem) or culture medium conditioned with intraluminal thrombus of human AAA (1:5 dilution) with or without HDL and LDL (100 μg/ml). At the end of the experiment, cell supernatants were aspirated, centrifuged for 5 min at 3.000 g and analyzed for fibronectin proteolytic fragments by Western blot. Remaining viable adherent cells were washed with PBS and assessed using the MTT test (3-[4,5-dimethylthiazol-2-yl]-2,5-diphenyltetrazolium bromide) as described. Alternatively, apoptosis was determined by the quantification of histone-associated DNA fragments using using a photometric enzyme immunoassay (Cell death detection ELISA$^P$-$_{LUS}$, Roche) following the manufacturer's instructions. Performing the Trypan blue exclusion test on trypsinized cells confirmed that 95% of remaining adherent cells did not exhibit membrane permeabilization.

Detection of Apoptosis in Situ

Human mammary arteries were obtained from patients undergoing cardiac surgery at Bichat Hospital (Paris, France). These tissues are considered as surgical waste in accordance with French ethical laws and the INSERM Ethics Committee. Equal segments of mammary arteries (5 mm rings), obtained by removal of the adventitia, were incubated with or without 10 nM elastase in the presence or absence of HDL or LDL (0.2 mg/mL each) for 24 hours in serum-free RPMI at 37° C. (5% CO2). After incubation of mammary endarteries with elastase, the tissue was fixed in 3.7% paraformaldehyde and embedded in paraffin. Immunohistochemistry was performed on 5 μm thick sections using a monoclonal antibody to single-stranded DNA (Apostain, Alexis) as a marker of apoptosis in situ.

Preparation of Conditioned Medium from AAA

Abdominal aortic aneurysm samples (AAA) were obtained from patients undergoing surgery, enrolled in the RESAA protocol (REflet Sanguin de l'évolutivité des Anévrysmes de l'Aorte abdominale). All patients gave their informed written consent, and the protocol was approved by a French ethics committee (CCPPRB, Cochin Hospital). AAA intraluminal thrombi sampled during surgery were incubated with 1 M acetate buffer, pH 4.5 (2 mL/g of wet tissue), for 2 hours at room temperature. Extracts containing elastase were then dialyzed against phosphate-buffered saline (PBS) for culture assays as previously described.

HDL Labeling with Carbocyanines

HDL was incubated overnight at 37° C. under gentle shaking with 10 μL/mL DiIC18 carbocyanines (Molecular Probes) and then separated by ultracentrifugation as described above. VSMCs were incubated with 100 μg/mL labelled-HDL for 8 hours. After three washes with PBS, cells were counterstained with DAPI (0.5 μg/mL for 10 minutes) and visualized under an epifluorescence microscope.

Immunocytofluorescence

Confocal microscopy: Human VSMCs were plated onto Labtek slides and incubated with 50 μg/mL HDL for 4 h. The slides were then washed with PBS, fixed with 4% paraformaldehyde, blocked in PSB-BSA 4%, incubated with goat anti-alpha-1 antitrypsin antibody and anti-ApoAI (Calbiochem) at a 1:50 dilution. Slides were then incubated with appropriate fluorescein 5-isothiocyanate (FITC) or tetramethyl Rhodamine isothiocyanate (TRITC) labeled secondary Ab (Sigma) at a 1:200 dilution for 1 h.

Amethyst Cohort

The AMETHYST (Aneurysm Metalloproteinases and Hypertension Study) is an ongoing study promoted by Inserm involving a cohort of patients with asymptomatic AAA (with an aortic diameter greater than 5 cm) scheduled for endovascular repair within 1 month. These patients were age-sex matched with healthy volunteers. All study participants gave informed consent.

The study was approved by the ethical committee (Cochin Hospital Comite de Protection des Personnes se Prétant à la Recherche Biomédicale, approval n° 1930 & 1931).

Exclusion criteria for patients were cancer, infection, and any immuno-mediated disease. Peripheral blood was drawn in standardized conditions (fasting subjects at rest for 10 min, between 8 and 10 am), with minimal stasis, into prechilled EDTA tubes. No later than 30 minutes after collection, two centrifugations were performed to separate the plasma from the blood cells (2500 rpm, 15 min, 12° C. and 2500 rpm, 15 min, 4° C.). Plasma samples were stored at −80° C. until used.

Determination of Apo A-I Concentration

Apolipoprotein A-I concentration was determined using an ELISA test from Mabtech AB (Nacka Strand, Sweden) according to the manufacturer's instructions.

Statistical Analysis

Statistical analysis was performed with GraphPAD InStat (GraphPAD Software). Concerning the comparison between AAA and age-gender matched controls, further adjustment for smoking habits was performed during the statistical analysis, without altering non-tobacco-adjusted comparison results. All experiments were performed at least 3 times. Results are expressed as mean±SD and were analyzed by ANOVA (differences were considered significant when $p<0.05$).

Results

HDL, but not LDL, Contains Alpha-1 Antitrypsin

The inventors used differential flotation properties of lipoproteins to isolate HDL by a two-step ultracentrifugation technique on KBr, similar to that used by Karls son et al. to identify alpha-1 antitrypsin (AAT) in HDL by a proteomic approach. The inventors have shown by Western blot that HDL isolated from plasma of 4 different subjects contains AAT whereas LDL isolated in the same conditions is devoid of this major plasma protein (FIG. 1A). Western-blot against alpha-2-antiplasmin performed on the same samples was not able to show the presence of this other abundant plasma protein either in LDL or in HDL. In spite of its high concentration in plasma, AAT is unlikely to be a contaminant co-isolated with HDL. Binding experiments were performed on ELISA plates coated with either Apo A-I or AAT. Apo A-I is able to bind to AAT but in a non-saturable fashion, suggesting a low affinity or non-specific binding. In a second step, the inventors tested the ability of HDL to trap more AAT. For this purpose the inventors incubated either HDL or LDL with purified AAT (1 mg:1 mg) for 16 hours at 37° C. under gentle agitation and then re-isolated both lipoproteins by ultracentrifugation, in order to get rid of free/unbound AAT. The inventor showed by Western Blot that HDL but not LDL is able to bind and incorporate additional AAT (FIG. 1B). The results indicate that in contrast to LDL, HDL possesses an affinity for AAT. Finally, the inventors have shown that AAT is more abundant in $HDL_3$ than $HDL_2$ fractions (FIG. 1C).

AAT is Present in Alpha-1 Fractions of HDL

In parallel, the inventors isolated HDL by selected-affinity immunosorbtion using an anti-apolipoprotein A-I column. Elution allowed recovery of the lipoprotein AI-containing fraction (LpAI). LpAI species were separated by nondenaturing two-dimension electrophoresis gels, allowing each particle containing Apo A-I to migrate according to its charge and size. The gels were either transblotted for Western blot analysis or stained by coomassie blue for subsequent proteomic analysis. Spectra containing a good series of y- and b-ions allowed for identification of peptides from AAT and Apo A-I. Mass spectrometry analysis performed on the different spots detected by colloidal coomassie blue staining identified AAT in alpha-1 particles ranging in diameter from 7 to 10 nm Stokes radii; as expected, Apo A-I was also identified in these particles. Twenty three unique AAT peptides were identified in the smallest 7 nm diameter particle while 3-4 peptides were identified in the other larger 8-10 nm particles, suggesting that the predominant LpAI AAT mass is localized in the 7 nm LpAI particle. Apo A-I composition in these particles varied, with fewer unique peptides identified in the 7 nm LpAI particles than in the larger 8-10 nm particles (8 vs 13-18, respectively). The 7 nm LpAI particle composition included lesser amounts of paroxonase, Apo A-IV, Apo D, Apo C-III, Factor V, and alpha-1-acid glycoprotein 1. Western Blot against AAT showed that the 7-10 nm particles of alpha-1 electrophoretic mobility contained AAT that co-localized with anti-Apo A-I staining, confirming the results obtained by mass spectrometry. The weak immuno-reactivity against Apo A-I on the blot is likely due to the fact that the antibody directed against Apo A-I do not react well on blots following 2D electrophoresis under non-denaturing conditions. AAT was also detected to a lesser extent in the large alpha fraction. Regular Western Blot following SDS-PAGE separation confirmed the presence of AAT only in LpAI isolated by the anti-AI column relative to a mock column without antibody. HDL isolated by ultracentrifugation from the same plasma was also positive for AAT.

HDL-Associated AAT Displays Anti-Elastase Activity In Vitro

In a second step, the inventors tested the potential of HDL-associated AAT to inhibit elastase activity. In vitro, leukocyte elastase (30 nM) was incubated with HDL isolated from healthy subjects and its activity was assessed using a chromogenic substrate, MeO-Suc-Ala-Ala-Pro-Val-pNa. Elastase was dose-dependently inhibited by HDL and almost total inhibition of elastase activity was reached ranging from 5-20 µg/mL HDL, depending on the batch of HDL (isolated from different healthy subjects). In contrast, 50 µg/mL of LDL from 3 different healthy subjects did not exhibit any anti-elastase activity (FIG. 2A). Similar results were obtained using conditioned media from luminal layers of human AAA intraluminal thrombi or supernatants of activated neutrophils as sources of leukocyte elastase. Both HDL and LDL were unable to inhibit plasmin activity (FIG. 2B).

HDL Prevents Elastase-Induced VSMC Anoikis

As described previously, purified leukocyte elastase or that present in the thrombus of abdominal aorta aneurysms (AAA) is able to induce detachment and subsequent death of human vascular smooth muscle cells (VSMCs) by degradation of the extracellular matrix (anoikis) The inventors used this model in order to test the potential of HDL to prevent detachment induced by leukocyte elastase. In FIG. 3 (A-C, E), the inventors show that VSMC viability was decreased by incubation with 10 nM elastase and that this effect was prevented in the presence of HDL, in a dose dependent manner (24±9 vs 98±2% for co-incubation with 100 µg/mL HDL p<0.005). However, LDL had no effect on VSMC detachment induced by elastase. In contrast to LDL, HDL was able to almost totally prevent fibronectin degradation induced by elastase, indicating a direct inhibition of pericellular matrix proteolysis (FIG. 3D). Next, the inventors assessed the protective effect of HDL on cells incubated with medium conditioned by the luminal layer of AAA intraluminal thrombus. The inventors have previously reported that leukocyte elastase was present chiefly in the luminal layer, relative to intermediate and abluminal layers of the AAA thrombus, and that it was able to induce detachment of VSMCs. The inventors show that HDL could thwart this phenomenon and inhibit apoptosis induced by incubation with conditioned medium from luminal layer of AAA thrombus (FIG. 3F, p<0.05). Finally, ex vivo incubation of mammary endarteries with elastase led to VSMC apoptosis, detectable within the tissue, and this effect was inhibited by co-incubation with HDL, but not with LDL. This is shown by the absence of nuclei positive for Apostain when mammary arteries were incubated with elastase in the presence of HDL (FIG. 3G).

Since HDL is known to exhibit anti-apoptotic effects that are not reported to be mediated by AAT, including intracellular effects, the inventors e tested whether pre-incubation of the VSMCs with HDL (pulse-chase) was sufficient to prevent apoptosis induced by elastase. The cells were incubated for either 4 or 16 hours with 100 µg/mL HDL, carefully rinsed thrice with PBS, and then incubated with 10 mM elastase (FIG. 4A). The inventors show that a remnant anti-apoptotic effect could be observed when cells where pre-treated for 16 hours by HDL (41±8.2% of inhibition). The inventors checked that HDL was internalized by the cells using red carbocyanine-labeled HDL (FIG. 4B) and showed by confocal miscroscopy that Apo AI colocalized with AAT within the cells (FIG. 4C).

HDL from Patients with AAA Carries Less AAT than Those from Healthy Subjects

As in other forms of atherothrombosis, it has been reported that levels of HDL were lower in AAA patients compared to normal subjects and that leukocyte elastase is involved in AAA pathophysiology. Here, the inventors report that AAA patients have significantly lower HDL than healthy controls (1.11 mmol/L±0.23, n=13 vs 1.35 mmol/L±0.3, p=0.017, n=23). Plasma apo A-I levels were also 68±2.6% lower in AAA patients relative to controls (FIG. 5A, p<0.0001). The inventors tested the hypothesis that HDL from patients with AAA could carry less AAT than those from control subjects. For this purpose, the inventors isolated HDL from each individual (AAA patients or matched controls) and assessed the presence of AAT by Western Blot, which was normalized to ApoAI content quantified by ELISA (29±0.59% reduction vs matched controls, p<0.0001). FIG. 5B shows that patients with aneurysms of diameter>5 cm have significantly less AAT associated with their HDL than the control group. Accordingly, elastase inhibitory potential associated with HDL was lower in patients than in controls (FIG. 5C) whereas global plasma anti-elastase activity was similar in the two groups (FIG. 5D), stressing on the importance of the compartmentalization tissue vs plasma.

In conclusion, the inventors report here a new antiprotease activity for HDL that is able to inhibit leukocyte elastase and its associated deleterious effects on vascular cells. The inventors showed that a decreased level of HDL and associated AAT in AAA patient may account for a less effective protection against elastase in the vascular wall, favoring the progression of this disease.

Example 2

HDL Enriched in AAT Reachs the Lung in Normal Mice and Prevent the Development of Emphysema In order to test the bio-availability of HDL in lung after intravenous injection, HDL were labeled with carbocyanines (red) (10 mg/kg). Two hours after injection, the mice were sacrificed; the lungs were embedded in OCT and frozen before sectioning. Immuno-staining was performed for AAT (green) and the nuclei counterstained with DAPI.

HDL purified from human plasma by ultracentrifugation was labeled by a fluorescent dye and tracked after IV injection. The injected HDL can reach the lung and can be detected from 2 to 48 hours following injection. Also, the maximal time after injection allowing detection of HDL in the lung was detected. After, the mice were sacrificed, both lung and liver were checked for accumulation of fluorescent HDL.

Method a/ Purification of HDL, Enrichment with AAT, Quality Controls

First, large amount of HDL purified from human plasma by ultracentrifugation was pooled in order to work with the same batch of HDL and HDL enriched with AAT. AAT was incubated for 16 hours at 37° C. under gentle agitation. Those HDL were then purified again by ultracentrifugation to eliminate free, unbound AAT. A Western-Blot for AAT and apolipoprotein A-I was performed on HDL and HDL loaded with AAT. Different amount of AAT were also analyzed by WB in order to assess the amount of AAT present in normal and enriched HDL (FIG. 6). Anti-elastase assay was performed in parallel, corroborating the results obtained by WB. These experiments quantify AAT in enriched HDL. The same amount of free AAT was then injected in a control group. The aim of this experiment is to test whether HDL-AAT prevent more the development of emphysema relative to AAT injected alone. HDL containing naturally AAT are also injected in another group.

Scheme of the Experiment

Elastase-treated mice were divided in four groups: injected with saline, HDL (75 mg/kg body weight), HDL enriched in AAT (75 mg/kg) or AAT alone (3.75 mg/kg) alone. HDL, HDL-AAT, AAT or saline were injected intravenously 2 hours after elastase injection and then 3 more times after 24, 48 and 36 hours.

Elastase used for intra-tracheal instillation was eliminated rapidly by the mouse (after one hour, there is no trace of elastase in the lung). The use of HDL comprising anti-elastase according to the invention is therefore inhibit endogenous elastase associated with neutrophil infiltration and not the elastase used to induce the emphysema.

45 mice are subjected to intra-tracheal elastase instillation. 15 mice are injected 4 times with saline during the first week following elastase treatment, and then 10 mice in each group were injected with HDL, HDL enriched in AAT or the same amount of AAT alone.

The mice were sacrificed 28 day after initial instillation of elastase, and the emphysema was semi-quantified by scoring alveoli destruction (double blind determination by two independent pathologists).

The average±SD is presented in the FIG. 7, showing that HDL-AAT protect by 40% the development of emphysema whereas HDL and AAT only show a mild protective effect (HDL-AAT vs saline: $p<0.001$, HDL-AAT vs HDL: $p=0.013$, AAT vs saline: $p=0.097$, HDL-AAT vs AAT: $p=0.112$).

Conclusion

The inventors have show that HDL enriched in AAT reaches the lung in normal mice and prevent the development of emphysema.

Example 3

Evaluation of HDL as a Vector of Antiprotease in Aneurysm of Abdominal Aorta (AAA)

AAA are a particular clinical manifestation of atherothrombosis localized in the abdominal part of the aorta, in which protease activities and especially elastase have been shown to be a driving force. Several evidences indicate that HDL can target atherosclerotic lesions where they act as cholesterol clearance particles. Gadolinium-HDL have been used as tracer for imaging atherosclerotic plaques.

The inventors show that injection of DiIC18-labelled HDL in apoE−/− mice results in a strong staining of the lipid core of atherosclerotic lesions from the aortic sinus.

Previous studies have demonstrated the feasibility of loading lipoproteins with drugs or proteins, especially in the field of cancer. The inventors have provided evidence of the involvement of two major serine proteases, plasmin and elastase, in the progression of complicated atherothrombotic disease such as aneurysms.

The inventors use HDL as carriers of inhibitors of plasmin and elastase.

Plasmin is generated from plasminogen by its activators (tissue-type (tPA) or urokinase (uPA)) both being active in complicated plaques. HDL is loaded with the following drugs and proteins before injection in a model of aneurysmal apoE-deficient mice, in order to evaluate their impact on atherothrombotic complications:

alpha-1 antitrypsin: is the natural inhibitor of neutrophil elastase, it was shown to be part of HDL and is easy to incorporate into reconstituted HDL particle, tranexamic acid: is a synthetic lysine derivative which exerts its antiplasmin effect by blocking in a reversible manner the lysine binding sites on plasminogen. This prevents plasminogen binding to tissue, fibrin or extracellular matrix and its subsequent conversion into plasmin.

The inventors have shown in example 1 that HDL can be loaded with AAT.

HDL-mediated antiprotease therapy is assessed in a model of apoE-deficient mice infused with angiotensin II.

ApoE−/− mice develop fatty streaks in the aortic root without atherothrombotic complications.

Several groups show that infusion of Ang II in these hyperlipidemic mice rapidly leads to the formation of complex lesions resulting in development of abdominal aortic aneurysms or of complicated vulnerable plaques.

These complicated lesions in mice exhibit many aspects of the human disease including medial degeneration, adventitial inflammation, mural thrombus or intraplaque hemorrhages.

In this model, these vulnerable lesions do not develop in the aortic root but in the descending aorta, providing evidence of an enhancement of proteolytic activity in the vessel wall.
Methods
Apo E$^{-/-}$-Ang II Mice Model Three- to 6-month-old male apoE−/− mice are subjected to a 4-week infusion of Ang II (1000 ng·kg−1·min−1) via subcutaneous osmotic minipumps (n=10). Two additional groups (n=10) are intravenously injected with and either HDL or HDL-enriched by alpha-1 antitrypsin.
HDL Loading with Alpha-1 Antitrypsin HDL isolated from healthy individual is incubated with commercial purified alpha-1 antitrypsin (1 mg/mL) at 37° C. for 16 hours under gentle agitation. HDL is then reisolated by ultracentrifugation (100,000 g overnight) after adjusting their density to 1.25 g/mL with KBr and overlay with saline/KBr solution (d=1.21). HDL fraction is recovered as a single band at the top of the tube and the KBr is eliminated by 3 washing steps using centrifugal filter devices. Western Blot analysis test the efficacy of alpha-1 antitrypsin enrichment.
Assessment of Plaque Rupture and Medial Degeneration Animals are euthanized, the abdominal and thoracic cavities are entered, blood drawn from the right ventricle, and the aorta are irrigated with PBS through the left ventricle. The abdominal aorta is exposed under dissection microscope, and the periadventitial tissue is carefully dissected away from the aorta wall. Maximal aortic diameter is determined with a digital caliper. The aortic root and heart is subsequently dissected out. The abdominal aorta (from the last intercostal artery to the ileal bifurcation) and the thoracic aorta are sectioned and weighed, and portions of these tissues are embedded in OCT for frozen section (determination of cell composition assessed by immunohistochemistry and oil-red O staining for assessment of lipids), or homogenized/sonicated for biochemical assays (determination of lipid content).
Conclusion HDL can deliver AAT and prevent aneurysm of abdominal aorta.

Example 4

Evaluation of the Protective Effects of HDL in a Rat Model of Stroke

Stroke is a leading cause of adult morbidity and mortality in Western countries. The only drug currently approved in the acute phase of stroke is the thrombolytic agent tPA. Use of tPA is limited to a very short therapeutic window, and also causes a 10-fold increase in symptomatic cerebral haemorrhage. Serine proteases (such as plasmin and tPA) and matrix metalloproteinases (MMP3, MMP9) have been shown to play a critical role in cerebral ischemia injury and haemorrhagic transformation, associated or not with tPA treatment.

The inventors, as already described by others, have demonstrated activation of MMP9 in the ischemic area in an embolic stroke model in the rat.

The inventors tested the hypothesis that injection of HDL during the acute stage of stroke could be neuroprotective.

The inventors have developed an embolic stroke model in rat (injection of a thrombus made ex-vivo into the middle cerebral artery).

Intravenous infusion of HDL in the acute stage of stroke resulted in a strong protective effect against subsequent ischemic damage.

Mortality at 24 hours after stroke was 41.6% in the placebo group versus 12.5% in the HDL-treated group (n=15 per group) p<0.05.

At 24 h, cerebral infarct volume median was 9.2% (IQR 4.6-15.6) in the HDL group versus 29.5% (12.9-66.6) in the placebo group (p<0.05).

The neurological deficit was decreased in the HDL group versus placebo and MMP9 (both pro- and active forms) was decreased significantly in the ischemic area after HDL therapy (FIGS. 8 and 9).

To elucidate the neuroprotective mechanisms of HDL in our stroke model, several hypotheses are tested; in particular, the inventors evaluate whether the presence of anti-elastase activity associated with HDL is important in the prevention of cerebral damage induced by the thrombus. The inventors also test the cytotoxicity of the thrombus on the blood brain barrier (BBB) and subsequent permeability using an in vitro model of BBB. The potential protecting effect of HDL on BBB is tested.

It is known that in addition to reversing cholesterol transport, HDL particles exert anti-inflammatory, antiprotease, and antithrombotic effects that may protect endothelial cells from acute injury. Administration of reconstituted HDL has been shown to normalize endothelial dysfunction in patients with hypercholesterolemia or with low HDL levels. Polymorphonuclear neutrophils (PMNs) play a key role in acute ischemic cerebral injury and in ischemiainduced BBB disruption, where their associated matrix metalloproteinase 9 (MMP-9) participates in BBB breakdown.

HDL inhibits cytokine-induced expression of endothelial adhesion molecules and hence reduces PMN adhesion and transmigration. The inventors thus hypothesized that HDL injection after the onset of stroke (0 to 5 hours) may decrease PMN recruitment in the ischemic area and also beneficial effects on cerebral damage after stroke.
Materials and Methods
Embolic Stroke Model Animal care and experimental protocols were approved by the Animal Ethics Committee of the University Paris 7, authorization 75-214. Male Sprague-Dawley rats weighing 300 to 350 g, were anesthetized with isoflurane mixed with air (4% for induction; 1% during surgery) under spontaneous respiration. Focal cerebral ischemia was induced by embolization of a preformed clot in the middle cerebral artery. Body temperature was maintained at 37° C._0.5 with a heating pad for the duration of surgery. Glycemia, arterial blood pressure, and blood gases were also monitored during surgery.
Sample Size Calculation The study was designed with 80% power to detect a relative 50% difference in cerebral infarct volume between groups (HDL versus placebo). Statistical testing was performed at the 2-tailed α level of 0.05 using a t test. Based on preliminary data indicating that infarct volume at 24 hours after stroke was median 42.1 (interquartile considering 25th to 75th percentile 17.6 to 65.0), the inventors used 17 rats per group.
Experimental Protocol Purified HDL (2 or 10 mg of Apo A-I/kg body weight), low-density lipoproteins (LDL, 10 mg apoB/kg body weight) or saline were administered intravenously to rats immediately after stroke onset (n=17 per group). Four supplemental groups received either saline or HDL (10 mg Apo A-I/kg body weight) 3 or 5 hours after stroke onset. One single intravenous injection was performed according to previously reported pharmacokinetics of HDL in rats. Computer-based randomization was used to allocate drug regimens to each group. Experiments were blinded and the operator was unaware of group allocation during surgery and outcome assessment.

The inventors evaluated the mortality rate and the neurological deficit at 24 hours after stroke onset using a modified Neurological Severity Score, which is a composite of motor, sensory, and balance tests.

Exclusion Criteria

Animals were excluded for analysis if the total lesion volume was _5% (n=3 in saline group, n=2 in LDL group, n=5 in HDL groups) or if subarachnoid hemorrhage was present (n=1 in HDL groups). No deaths due to anesthesia or surgery occurred within 3 hours of embolic stroke induction.

Measurement of Infarct Volume and Brain Edema

Rats were euthanized 24 hours after induction of focal ischemia. Seven coronal sections of the brain (2 mm in thickness) were stained with 2% 2,3,5-triphenyltetrazolium chloride (Sigma-Aldrich) for 20 minutes at room temperature. The infarct volume in animals that died before the 24-hour time point was also evaluated and included in the results. Volume calculation with edema correction were performed blindly using the following formula:

$$100 \times (\text{contralateral hemisphere volume} - \text{noninfarct ipsilateral hemisphere volume}) / \text{contralateral hemisphere volume.}$$

Brain edema was determined by calculating the volume difference between the 2 hemispheres and dividing by the volume of the left hemisphere. All the ancillary experiments (Evans blue and immunostaining) were performed on additional animals, except for zymography (which is compatible with prior 2,3,5-triphenyltetrazolium chloride staining).

HDL and LDL Preparation

HDL and LDL were isolated from a pool of plasma from healthy volunteers by ultracentrifugation as described previously.14 Apoprotein B and apoprotein A1 concentrations were determined by immunonephelometry and did not show any crosscontamination between HDL and LDL. Five different batches of HDL were used for the study. The purity of LDL and HDL fractions (absence of albumin contamination) was verified by sodium dodecyl sulfate-polyacrylamide gel electrophoresis followed by Coomassie blue staining.

HDL Labeling with Carbocyanines and Tracking In Vivo

HDL was incubated overnight at 37° C. under gentle shaking with 8.5_g/mL DiIC18 carbocyanines (Molecular Probes Inc) and then separated by ultracentrifugation. Labeled HDL (10 mg Apo A-I/kg) was administered intravenously immediately after stroke onset (n=6) and fluorescein isothiocyanate-dextran (2000 kDa; Sigma-Aldrich) was injected just before euthanasia (n=3). After decapitation, brain sections were embedded in optimal cutting temperature medium and immediately frozen. Coronal sections (8_µm; at 0.70 mm posterior to bregma) were prepared with the use of a cryostat. Cell nuclei were stained with 4,6-diamidino-2-phenylindole (0.5 µg/mL for 10 minutes) and the sections were observed under an epifluorescence microscope.

Alanine Transaminase and Aspartate Aminotransferase Quantification for Assessment of Hepatic Function Blood was sampled at baseline, 1, 3, and 24 hours after stroke onset in each group (n=4 per group). The plasma activities of alanine and aspartate aminotransferase were measured by commercially available kits using an Olympus AU400 spectrophotometer.

Evans Blue Extravasation

BBB permeability was quantitatively evaluated using fluorescence detection of extravasated Evans blue dye. Rats were treated by HDL (10 mg/kg) or saline immediately after stroke induction (n=6 per group). Two percent Evans blue in saline was then infused (4 mL/kg intravenously) 24 hours after clot injection. After 3 hours, rats were deeply anesthetized with pentobarbital and transcardially perfused with saline to wash out the intravascular dye. Brains were removed, cut into 2-mm coronal sections, embedded in optimal cutting temperature, and frozen. Ten-micron sections (at _0.70 mm posterior to bregma) were prepared. Evans blue extravasation was observed by fluorescence microscopy and was quantified semiautomatically with morphometry software (Histolab 6.1.5; Microvision Instruments).

Immunohistochemistry

Frozen sections were fixed with 3.7% paraformaldehyde and blocked with 10% goat serum. Sections were incubated overnight at 4° C. with primary antibodies. A mouse monoclonal antirat endothelial cell antigen antibody (2.5 µg/mL; Serotec) was used to detect vessels, a polyclonal rabbit anti-myeloperoxidase (16.5 µg/mL; Dako) to detect PMNs, an antiglial fibrillary acidic protein (5.8 µg/mL; Dakocytomation) to detect astrocytes, and an anti-NF200 (17 µg/mL; Sigma-Aldrich) to visualize neurons. A monoclonal mouse antirat intercellular adhesion molecule-1 (10 µg/mL; Biolegend) was also used. The inventors included non-immune IgG in each set of experiments as the primary antibody to test the specificity of the signal and used Alexa-Fluor 488 or 555 as secondary antibodies. Immunostaining was analyzed with a fluorescent microscope interfaced with a digital capture system. The number of immunostained cells was determined semi automatically with morphometry software (Histolab 6.1.5; Microvision Instruments). All immunohistological evaluations were carried out by an observer who was blinded to the treatment.

Gelatin Zymography

Sodium Dodecyl Sulfate-Polyacrylamide Gel Electrophoresis Gelatin Zymography

Immediately after decapitation and brain removal, ipsilateral ischemic brain tissue and the corresponding contralateralnonischemic area were carefully dissected out and separately incubated in RPMI 1640 (10 µL/µg wet tissue) containing antibiotics and antimycotics (Gibco) for 24 hours at 37° C. to collect proteases released by the brain tissue (n=7). After centrifugation (3000 g, 10 minutes, 20° C.), equal volumes of conditioned medium were electrophoresed in the presence of 0.2% sodium dodecyl sulfate in 10% polyacrylamide gels containing 2.5 mg/mL gelatin under nonreducing conditions. Gelatinolytic activity was quantified by densitometry using National Institutes of Health Image 1.42q software.

In Situ Zymography

Ten-micron coronal sections (at +0.70 mm posterior to bregma) were preincubated with either phosphate-buffered saline alone or with 10 mmol/L 1,10-phenanthroline (a broad range MMP inhibitor) for 2 hours at room temperature. They were then incubated with the fluorogenic substrate DQ-Gelatin (40 µg/L; Molecular Probes) in zymography buffer: 50 mmol/L Tris-HCl, pH 7.6, 150 mmol/L NaCl, 5 mmol/L CaCl2, 200_µmol/L sodium azide for 2 hours at 37° C., followed by 10% neutral formalin fixation (n=4 per group). Proteolytic activity was detected as green fluorescence using an epifluorescence microscope. A control section was incubated in zymography buffer without DQ-Gelatin to detect possible tissue autofluorescence.

Statistical Analysis

Data are presented as medians (quartiles) for continuous variables and percentages for qualitative variables. The inventors analyzed data by either a Mann-Whitney U test or, in cases in which >1 group is compared, a Kruskal-Wallis test followed, and if P<0.05, by a Mann-Whitney U test. Comparison of mortality between groups was performed using the Fisher exact test. A 2-tailed value of P<0.05 was considered significant. Data were analyzed using JMP 7.0.1.

Results

Volume, and Neurological Deficit

Compared with saline injection, intravenous administration of HDL immediately after the onset of stroke significantly decreased stroke-related deaths at 24 hours. A dose effect was observed with a 68.4% reduction in death rate for a dose of 10 mg/kg (P=0.015). Relative to saline-treated controls, administration of HDL also significantly reduced infarct size immediately after stroke (P=0.0003) and at 3 and 5 hours (P=0.011 and P=0.019, respectively). This protective effect was dose-dependent Accordingly, the neurological deficit at 24 hours after stroke onset was decreased in the HDL-treated group (P=0.015). Purified LDL did not reduce infarct size or stroke-related death relative to the saline-injected group (P=0.75 and P=0.66, respectively). Because HDL has been reported to induce hepatic damage, the inventors assessed circulating hepatic enzyme levels; plasma levels of aspartate aminotransferase and alanine aminotransferase taken during the first 24 hours after stroke did not differ after HDL infusion compared with baseline.

HDL Decreased BBB Breakdown and Brain Edema

The inventors measured Evans blue extravasation in the infarct area at 24 hours after stroke onset. Morphometric quantificationrevealed that HDL (10 mg/kg) reduced BBB permeability by 64% compared with control (P=0.0066). Brain edema was significantly decreased in the HDL treated group (10 mg/kg) relative to the saline-treated group (18.1% versus 5.7%, respectively; P=0.01).

Labeled HDL Penetrated the Infarct Area

To test whether HDL administration may reach the infarct area and thus directly impact the endothelium, the inventors injected fluorescently labeled HDL immediately after stroke onset. Twenty-four hours later, the rats were injected intravenously with the vascular marker fluorescein isothiocyanate-dextran which was allowed to circulate for 10 seconds before euthanasia. HDL could penetrate the infarct area and be taken up by endothelial cells and by astrocytes, but no colocalization with neurons was observed.

HDL Reduced PMN Recruitment and Associated MMP Gelatinase Activity in the Infarct Area Myeloperoxidase immunostaining followed by morphometric quantification (number of myeloperoxidase-positive cells) revealed that injection of 10 mg/kg HDL decreased PMN recruitment by 70% relative to saline-treated controls (P=0.027). In situ zymography showed an increase in the overall gelatinase activity in the ipsilateral infarct area compared with the homologous contralateral control area. After HDL administration, this increase in gelatinase activity appeared less important than in the saline-treated group. At 24 hours after stroke onset, sodium dodecyl sulfate-polyacrylamide gel electrophoresis gelatin zymography showed an increased activity of MMP-9 in the ischemic area versus the contralateral noninfarcted area. MMP-9 activity was reduced in the infarct area in the HDL-treated group compared with the control group. Similar results were obtained for the neutrophil-associated homodimeric form of MMP-9.

HDL Decreased Intercellular Adhesion Molecule-1-Positive Vessels in the Infarct Area The inventors postulated that decreased PMN recruitment in the HDL treated group may be due to a reduced expression of intercellular adhesion molecule-1 (ICAM-1). Immunostaining for ICAM-1 revealed a decrease in ICAM-1-positive vessels in the HDL-treated group compared with controls.

This study thus showed a beneficial effect of HDL against cerebrovascular ischemia. As shown by immunostaining, HDL is taken up by endothelial cells and glial cells but not neurones. To the knowledge of the inventors, neuroprotective effect of HDL has been reported, but this effect was preventive since HDL was injected 2 hours before the onset of stroke. By contrast, the inventors injected HDL up to 5 hours after the onset of cerebral ischemia. Such injection provided therapeutic neuro and vasculoprotective effect.

Example 5

HDL in Stabilization of Neovessels in Atherothrombosis

Accumulation of neutrophils, which are the first phagocytic cells in acute innate response, was reported at the site of plaque rupture and neutrophil infiltrates are present in culprit lesions in acute coronary syndromes. Intraplaque hemorrhage has been shown to be associated with enrichment in neutrophils and neutrophils-derived proteases in the plaque. This information indicates that neutrophils participate in mechanisms leading to plaque rupture. Neutrophils destabilize neovessels in atherosclerotic plaques through various mechanisms. Neutrophils endocytose foreign material, produce potent reactive oxygen species, and release a variety of proteolytic enzymes, such as elastase, cathepsins, MMP-8 and -9, and myeloperoxidase, which help to clear infections, but also participate in tissue degradation and destruction. Leukocyte-derived serine protease activities are found in unstable areas in carotid endarterectomy specimens. This indicates that excessive leukocytes-mediated ECM proteolysis is causally involved in plaque destabilization. Extracellular matrix proteolysis by plasmin and by elastase induces apoptosis of vascular smooth muscle cells that are crucial cells stabilizing the plaque.

In addition to their ability to provoke mesenchymatous cell detachment and death (anoïkis), leukocytes-derived proteolytic activities also impair the maturation of neoangiogenic vessels in atherosthrombotic plaques through degradation of pro- and anti-angiogenic factors.

To investigate the potential deleterious effects of neutrophils-derived proteases on blood vessels growth and stability, in vitro and in vivo models of angiogenesis are used. The effect of resting and activated neutrophils on the formation of capillary-like structures from rat aortic ring and from human mammary arteries in Matrigel supplementedis is compared with or without inhibitors of neutrophils-derived proteases.

The effect of neutrophils on the stability and viability of immature blood vessel by adding resting or activated neutrophils to the Matrigel at a later time point, once capillary-like structures have already formed is studied.

Similar experiments are performed using conditioned media from either complicated or non-complicated plaques from human carotid artery instead of purified neutrophils.

In parallel to these in vitro studies, in vivo experiments are performed as follows. Growth factor-loaded Matrigels are implanted in dorsal skinfold chambers to induce angiogenesis locally.

The angiogenic vessels are acutely and locally stimulated with conditioned media from complicated or non-complicated plaques, in the presence or absence of proteases inhibitors.

Modifications in the permeability of angiogenic vessels and incidence of hemorrhages in Matrigels are observed by intravital microscopy.

A mouse model of plaque rupture was developed and in this model, a ligature is combined to the placement of a perivascular cuff on the carotid artery in apoE−/− mice. This results in a lipid- and collagen-rich lesion that contains a number of macrophages, T lymphocytes, and smooth muscle cells. Subsequently, the cuff placement evoked intraplaque hemorrhage and plaque rupture with fibrin(ogen)-positive luminal thrombus. To address the role of neutrophils in intraplaque hemorrhage in vivo, neutrophils is depleted and intraplaque hemorrhage and plaque rupture in these mice is prevented.

HDL therapy in both models (angiogenesis-skinfold chamber and model of plaque rupture) is tested.

First, the potential stabilization of neovessels by HDL in the skin-chamber model since injection of elastase is tested, conditioned media from atherothrombotic plaques and HDL is much better controlled.

In case of a prevention of hemorrhage induced by elastase (purified, that contained in neutrophils or in the plaque), injection of HDL, enriched or not with alpha-1 antitrypsin are tested in the mouse model of plaque rupture.

Conclusion

The inventors show in this experiment that HDL therapy is useful in the stabilization of neovessels.

Example 6

Protective Effect of HDL on Blood Brain Barrier Permeability Induced by Neutrophils Under Ischemic Conditions a) Protective Effect of HDL Isolated from Plasma of Healthy Subjects The blood brain barrier (BBB) is a biological filter designed to segregate the vascular compartment from the central nervous system (CNS), in which endothelial cells play a pivotal role. Breakdown or dysfunction of the BBB is a key step associated with several vascular and degenerative diseases of CNS (tumours, epilepsy or ischemia stroke).

Ischemia-induced BBB breakdown allows entering of deleterious blood elements into the cerebral compartment, such as circulating leukocytes and their secretion products including proteases, which may increase the risk of hemorrhagic transformation and/or cerebral oedema. The inventors investigated the effects of neutrophils and elastase on BBB, under ischemic conditions (OGD: Oxygen and Glucose Deprivation), and the possible protective effect of HDL (High Density Lipoproteins).

Materials and Methods

The permeability of the BBB was tested using an in vitro model of human cerebral endothelial cells consisting of human immortalized cerebral endothelial cells (B B Weksler et al. Blood-brain barrier-specific properties of a human adult brain endothelial cell line, FASEB J. 2005 November; 19(13): 1872-4.) cultured on transwell by adding Dextran-FITC 70 kDa in the upper compartment and measuring fluorescence in the lower compartment after 4 h of OGD conditions.

The coefficient of permeability was calculated as previously reported (B B Weksler et al.). Such a model of blood brain barrier allowed thet investigation of the effect of elastase and of neutrophils on permeability under normal or ischemic conditions.

Western Blot with specific antibodies directed against cell junction proteins or extracellular matrix proteins allowed assessment of proteolysis induced by neutrophils or purified elastase in the presence or not of HDL. HDL were isolated from plasma of healthy volunteers by ultracentrifugation.

Results

The in vitro BBB model expresses cell junction proteins (VE-Cadherin) and tight junction proteins (JAM-1, ZO-1). These proteins are degraded when the BBB is incubated with elastase or with the supernatant of activated neutrophils, leading to an increased permeability of the BBB.

After 4 hours of OGD conditions, the permeability was not significantly affected. Only incubation with elastase and neutrophils under OGD conditions increased significantly the permeability relative to OGD conditions alone or under normoxic conditions Addition of HDL prevented proteolysis and limited the permeability ((FIG. 10). The results indicate that elastase (purified or that contained in neutrophils) and OGD conditions have deleterious effects on the BBB, which can be prevented by HDL.

The inventors have thus shown that HDL (purified from human plasma) were able to inhibit significantly this protease-mediated increase in BBB permeability in ischemic conditions. Therefore, the inventors put in light the fact that ischemia promotes neutrophil degranulation and that alpha-1-antitryspin (AAT) associated with HDL could prevent the damages of elastase on the BBB.

b) rHDL are Taken Up by Cerebral Endothelial Cells

Reconstituted HDL (CSL111) or HDL isolated from plasma of healthy donors (HDL) were labelled with DiIC18-carbocyanines and then incubated with cerebral endothelial cells for 4 hours. The inventors proceeded to stainings as follows:

Nuclei were stained by DAPI; and
HDL were labelled by carbocyanine (DiIC18).

Both type of HDL were taken up by endothelial cells indicating a potential intracellular effect of HDL associated with their protection of permeability induced by proteases under ischemic conditions.

A recent study reports that elastase is able to be internalize in various cell types and then degrade intracellular substrates within the cell (A M Houghton et al., *Neutrophil elastase-mediated degradation of IRS-1 accelerates lung tumor growth*, Nat Med. 2010 February; 16(2):219-23).

Therefore, use of HDL or rHDL is a very promising strategy to counteract intracellular effects of elastase.

Example 7

Loaded Reconstituted HDL (rHDL)

The feasibility of rHDL enrichment by AAT was tested using CSL111 and Zemaira (CSL Behring).

Materials and Methods

Reconstituted HDL (rHDL) were incubated with AAT with or without a fluorescent dye (DiIC18 <<carbocyanine>>) for 2 hours at 37° C. under gentle agitation. After ultracentrifugation on gradient of KBr, rHDL could be isolated at a density of 1.1 after adjusting the initial density to 1.15 and overlay with d=1.1 and finally d=1 (100,000 g for 16 hours at 20° C.).

Results

After ultracentrifugation, enrichment with AAT produces a white band, visible directly in the ultracentrifugation tube without fluorescent dye and not observed in AAT alone (without incubation with rHDL).

After reisolation of rHDL by ultracentifugation, a silver nitrate staining is performed after SDS-PAGE (FIG. 11). Said staining shows enrichment of HDL with AAT (central lane) after re-isolation of rHDL by ultracentrifugation.

The inventors thus enlightened the fact that rHDL can be enriched in an agent such as AAT.

Example 8

Protective Effect of Intravenous Injection of HDL after Treatment with rtPA in Rats Suffering from Stroke Recombinant tissue plasminogen activator (rtPA) is the only drug approved and used in humans that dissolves embolic clots in stroke. However, rtPA is a protease reported to display deleterious effects on the blood brain barrier (BBB), increasing the risk of hemorrhagic complications. The inventors tested whether HDL are still able to reduce the infarct volume in the presence of rtPA, in order to simulate the clinical situation in case HDL would be used for therapeutics of stroke in humans.

Materials and Methods

Animal care and experimental protocols were approved by the Animal Ethics Committee of the INSERM-University Paris 7, authorization 75-214. Male Sprague-Dawley rats (Janvier, France) weighing 300 to 350 g, were anesthetized with isoflurane mixed with air (4% for induction; 1% during surgery), under spontaneous respiration. Focal cerebral ischemia was induced by intraluminal suture occlusion of the middle cerebral artery for 4 hours30. Physiological saline (2.0 mL/kg body weight) with or without recombinant tPA (10 mg/kg body weight; Genetech) was administered (10% bolus, 90% continuous infusion) to rats through the right femoral vein. The relatively high dose of tPA was necessary to achieve a fibrinolytic effect in rats similar to that of thrombolytic therapy in humans (W Liu W et al. *Normobaric hyperoxia reduces the neurovascular complications associated with delayed tissue plasminogen activator treatment in a rat model of focal cerebral ischemia* Stroke. 2009 July; 40(7): 2526-31). The tPA or saline treatment was started immediately before reperfusion and continued for 30 minutes after withdrawal of the suture. This regimen assured that the reperfused tissue was exposed to the agent. After saline or tPA administration, rats were returned to their cages.

Animals were assigned to 1 of 4 groups (n=10 per group): control (saline treatment only); t-PA alone (10 mg/kg); HDL alone (10 mg/kg IV, jugular vein); and t-PA plus HDL. HDL 10 mg/kg IV was injected 5 minutes before the onset of reperfusion. Sacrifice for infarct measurement occurred 24 hours after stroke. Body temperature was maintained at 37° C.+/−0.5 with a heating pad for the duration of surgery. Glycemia, arterial blood pressure and blood gases were also monitored during surgery.

Results

The infarct volume was significantly decreased in rats treated by HDL at the time of rtPA injection (FIG. 12A)

The presence of hemorrhage was evaluated macroscopically. The incidence of hemorrhage induced by rt-PA was reduced in rats co-treated by rtPA+HDL (75% versus 50%) (FIG. 12B).

The inventors have thus shown that injection of HDL provide protection on the BBB and thus alleviate the deleterious effect of injection of Recombinant tissue plasminogen activator (rtPA) by reducing the risk of hemorrhagic complications.

Example 9

HDL-Based Therapy Reduces Hemorrhagic Transformation-Induced by Tissue Plasminogen Activator Treatment in Experimental Stroke The inventors showed in example 9 that intravenous injection of high density lipoproteins (HDL) was neuroprotective in an embolic stroke model. They thus hypothesized that HDL vasculoprotective actions on the BBB may decrease hemorrhagic transformation (HT)-associated with tPA administration at the acute stage of stroke. For corroborating such hypothesis, they used HDL alone or in combination with tPA on HT in vivo in two models of focal middle cerebral artery occlusion (MCAO, embolic and transient monofilament ischemia), and in vitro on a model of BBB. Sprague-Dawley rats were submitted to a transient MCAO (embolic or 4 hours by a monofilament). The rats were then randomly injected by tPA (10 mg/kg) or saline with or without HDL purified from human plasma (10 mg/kg). The effects of HDL were assessed blindly 24 hours later by evaluating mortality rate, neurological deficit score and infarct size. The hemorrhagic transformation was also assessed. The BBB integrity was evaluated by immunostaining of collagen IV and immunoglobulin G extravasation. The integrity of the BBB was tested using an in vitro model of human cerebral endothelial cells.

Material and Methods

Animal Procedures and Experimental Design

STAIR recommendations have been followed to avoid bias due to experimental design 10. Animal care and experimental protocols were approved by the Animal Ethics Committee of the INSERM-University Paris 7. Male Sprague-Dawley rats (Janvier, France) weighing 300 to 350 g, were anesthetized by isoflurane mixed with air (4% for induction; 1% during surgery), under spontaneous respiration. Two different models of focal cerebral ischemia were used as requested by STAIR recommendations: embolic (eMCAO) and transient filament MCAO (fMCAO). Focal cerebral ischemia was induced by intraluminal occlusion of the middle cerebral artery for 4 hours. eMCAO was induced by injection of a preformed clot at the origin of MCA as already described. Continuous laser Doppler flowmetry (VMS, Moor Instrument) was used to monitor regional cerebral perfusion to ensure the adequacy of filament MCA occlusion (perfusion decreased to <20% of preischemic baselines). Animals were assigned to 1 of 4 groups (n=12 per group): control (saline treatment only); tPA alone (10 mg/kg); HDL alone (10 mg/kg IV, jugular vein); and tPA plus HDL. One single intravenous injection was performed according previously reported pharmacokinetics of HDL in rats. Saline (2.0 mL/kg body weight) with or without recombinant tPA (10 mg/kg body weight; Actilyse, Boehringer Ingelheim) was administered (10% bolus, 90% continuous infusion) to rats via the right femoral vein. The relatively high dose of tPA was necessary to achieve a fibrinolytic effect in rats similar to that of thrombolytic therapy in humans. Continuous tPA or saline infusion (for 30 min. Harvard Apparatus Infusion Pump) started 4 hours after stroke onset, immediately before recanalization (after withdrawal of the filament in fMCAO), or 4 hours after clot placement in the MCA. After saline or tPA administration, rats were returned to their cages. Body temperature was maintained at 37° C.±0.5 with a heating pad for the duration of surgery. Glycemia, arterial blood pressure and blood gases were also monitored during surgery. Mortality rate was determined at 24 hours. Neurological deficit were determined on the remaining rats using a modified Neurological Severity Score which is a composite of motor, sensory and balance tests. Computer-based randomization was used to allocate drug regimens to each group. Experiments were blinded and the operator was unaware of group allocation during surgery and outcome assessment.

Exclusion Criteria

Animals were excluded for analysis if the total lesion volume was <5% (n=4 in eMCAO); subarachnoid haemorrhage (n=1 in eMCAO and 2 in fMCAO), inadequacy of MCA occlusion, n=3 in eMCAO and 1 in fMCAO. One death due to anaesthesia or surgery occurred within 4 hours of stroke induction (1 in fMCAO).

Measurement of Infarct Volume, and Intracranial Hemorrhage

Rats were euthanized 24 hours after induction of focal ischemia. Seven coronal sections of the brain (2 mm in thickness) were stained with 2% 2,3,5-triphenyltetrazolium chloride (TTC, Sigma-Aldrich) for 20 minutes at room temperature. The brain infarct volumes of animals that died before the 24 hours were also evaluated and included in the results. Volume calculation with oedema correction was performed blindly using the following formula: 100× (contralateral hemisphere volume−non infarct ipsilateral hemisphere volume)/contralateral hemisphere volume. Intracerebral hemorrhage was classified before TTC staining by an examiner unaware of the regimen group in three groups: no hemorrhage (0), hemorrhagic infarction (H), defined as individual of several petechiae in the core or at the borders of the ischemic area, and parenchymal hematoma (P) when a large area of blood was observed within the core of the infarct. Ten-micrometer sections were cut from the caudal site of all 7 slices and analyzed before TTC staining. Areas of hemorrhagic transformation from these 7 brain sections were measured using Photoshop software by semi-automatic selection of extravasated erythrocytes.

IgG Extravasation

Blood-brain barrier permeability was evaluated in vivo by using fluorescence detection of IgG extravasation in filament MCAO model. At 24 hours after stroke, rats were deeply anesthetized with pentobarbital and transcardially perfused with saline. Brains were removed, cut in 2 mm coronal sections, embedded with OCT and frozen. Ten μm sections (at +0.70 mm posterior to bregma) were prepared. Sections were prepared and incubated overnight at 4° C. with donkey anti-rat IgG antibodies (5 μg/mL, Molecular Probes) labelled with Alexa Fluor® 488. IgG extravasation was quantified semi-automatically with morphometry software (Histolab 6.1.5, Microvision Instruments).

Immunohistochemistry

Frozen sections were fixed with 3.7% paraformaldehyde and blocked with 10% goat serum. Sections were incubated overnight at 4° C. with a rabbit polyclonal to collagen IV (2 μg/mL, Abcam) for detection of basal lamina of intracerebral vessels. FITC-conjugated Bandeiraea Simplicifolia Lectin I (isolectin B4) (5 μg/mL, Vector Laboratories) was used to visualize endothelial cells. Non-immune rabbit IgG were included in each set of experiments as primary antibody to test the specificity of the signal. We used Alexa-Fluor® 555 as secondary antibodies. Immunostaining was analysed with a fluorescent microscope interfaced with a digital capture system. All immunohistological evaluations were carried out by an observer who was blinded to the treatment. For semi-quantification of the collagen type IV expression, three fields of each territory were acquired using a×10 objective. A threshold of fluorescence intensity, which encompasses positive vessels on the contralateral image, was applied to each corresponding ipsilateral image. IHC analysis was performed in filament MCAO model.

Sample Size Calculation

The study was designed with 80% power to detect a relative 50% difference in the prevalence of parenchymal hematoma between groups (tPA+HDL versus HDL). Statistical testing was performed at the two-tailed [alpha] level of 0.05 using a t test. Based on preliminary data, 12 rats per group were needed.

Isolation of Lipoproteins

Lipoproteins were isolated from a pool of heparinized plasma of healthy volunteers by ultracentrifugation. In brief, plasma density was adjusted to d=1.22 with KBr and overlaid with KBr saline solution (d=1.063). Ultracentrifugation was performed at 100,000 g for 20 h at 10° C. The density of the bottom fraction containing HDL was adjusted to 1.25 with KBr and overlaid with KBr saline solution (d=1.22). The second ultracentrifugation was performed at 100.000 g overnight at 10° C. After this step, HDL fractions, representing the top layer of the tube, were recovered as a single band, and were then extensively rinsed with saline and concentrated using a centrifugal concentrating device (cutoff 10 kDa; Vivascience, Stonehouse, UK). All fractions were desalted either by dialysis against saline or by centrifugation and 3 washes with saline. For tracking in vivo, HDL were labelled with carbocyanines. HDL were incubated overnight at 37° C. under gentle shaking with 8.5 μg/mL DiIC18 carbocyanines (Molecular Probes Inc., USA) and then separated by ultracentrifugation. Labelled HDL (10 mg apoA1/kg) were administered intravenously in filament MCAO model (4 hours of MCAO) immediately after stroke onset (n=3). Rats were euthanized at 1, 3 and 24 hours after stroke onset. After decapitation, brain sections were embedded in optimal cutting temperature (OCT) medium and immediately frozen. Coronal sections (8 μm) (at +0.70 mm posterior to bregma) were prepared with the use of a cryostat. Isolectin B4 (Vector Laboratories) was used to identify endothelial cells as already described. Cell nuclei were stained with 4',6'-diamidino-2-phenylindole (DAPI) (0.5 μg/mL for 10 minutes) and the sections were observed under an epifluorescence microscope.

Effect of HDL on tPA Activity.

The potential effect of HDL on tPA activity was measured in vitro using recombinant tPA or ex vivo on plasma after injection of tPA±HDL. The amidolytic activity of tPA (400 μg/mL) was assessed by using SPECTROZYME® chromogenic substrate (Methylsulfonyl-D-cyclohexyltyrosyl-glycyl-arginine paranitroaniline acetate, America Diagnostica) P-444 substrate in the presence or absence of HDL (0.4 g/mL). Kinetic of amidolysis by tPA with 1 mM SPECTROZYME® chromogenic substrate at 37° C. was monitored by measuring absorbance at 405 nm for 2 hours with a multiscan spectrophotometer (BMG, Labtech). Initial rates of tPA (mDO/min) were calculated from plots of 405 nm versus time which were proportional to the tPA activity. For ex vivo experiments, tPA (10 mg/kg) was administered by IV femoral injection (10% bolus, and 90% during 20 min) in rats with or without HDL (10 mg/kg). Blood collection was perfomed at the jugular vein in citrate-containing tubes, 3 min after tPA, HDL or tPA+HDL administration. Plasma samples were 20-fold diluted with phosphate buffered saline containing 0.1% human serum albumin (AbCys) and 0.01% Tween20 in 96-well microtiter plates. tPA amidolytic activity was determined as described above. Measurements were performed in triplicate (n=3 per group of rats) and expressed as mean±SD.

In Vitro Blood-Brain Barrier Model.

Cell Culture

The human brain endothelial cell line hCMEC/D3 kindly provided by Dr. P. O. Couraud. Cells were cultured in complete EBM-2 medium (Endothelial Basal Medium+2.5% of fetal calf serum and supplements containing hydrocortisone and growth factors).

Cells Treatments

Before each experiment, cells were washed 3 times with PBS and then incubated with 200 nM tPA and/or 400 μg/mL of HDL. OGD (Oxygen Glucose Deprivation) conditions were obtained by using DMEM medium without glucose (Gibco) versus 1 g/L glucose DMEM for non-OGD conditions. Oxygen deprivation was obtained by using a hypoxia chamber (Billups-Rothenberg) where atmospheric air was replaced by a mix of gas (0% O2, 5% CO2, 95% N2, Air Product). DMEM used for OGD conditions was equilibrated with the same mix.

In Vitro Permeability Measurements

For permeability experiments, hCMEC/D3 cells were seeded at $5.105$ cells/cm$^2$ on collagen inserts (PCF filters, 0.4 µm pore size, Millicell 24-well plates, Millipore) in complete EBM-2. Cells were grown for 14 days post-confluence before use. Permeability was assessed using fluorescein isothiocyanate (FITC) labelled dextran (70 kDa molecular weight). FITC-dextran (0.385 mg/mL) was added to the inserts, which were transferred every 15 minutes for 45 minutes to collecting wells containing 600 µL of fresh medium. 200 µL from the collecting wells were transferred into a 96-well plate, and the dextran fluorescence was determined on the microplate reader at 485 nm (excitation) and 538 nm (emission). Fluorescence was converted to concentration using a standard curve. The volume cleared was calculated from the ratio of dextran concentration in each sample to the applied concentration (0.385 mg/mL). The endothelial permeability coefficient Pe (cm/min) was calculated by determining the volumes of clearance of dextran with or without cells. The cleared volume was calculated from the ratio of initial dextran concentration (0.385 mg/mL) to that in the collecting wells, and plotted against time. PS (permeability surface) was calculated from $1/PS=1/PSe-1/PSf$, where PSe is the slope of clearance in the presence of cells and PSf is the slope for a blank insert (cell free)16. Pe=PS/S, where S is the surface area of the insert (0.7 cm$^2$).

Immunocytofluorencence

HCMEC/D3 cells were seeded at $5.105$ cells/cm$^2$ onto collagen-coated labteks in complete EBM2. Cells were grown for 7 days post-confluence before use. After treatments, cells were fixed in 3.7% paraformaldehyde for 30 minutes and stored in PBS at 4° C. Rabbit polyclonal anti-human VE-Cadherin (1:200; Bender Med Systems) was used as primary antibody, followed by a secondary antibody conjugated to Alexa 555 (Invitrogen). Negative controls using non-immune rabbit IgGs at the same concentration as anti-VE cadherin were included in each set of experiments to check for nonspecific staining.

Western Blot Analysis of Fibronectin

For detection of fibronectin in HCMEC/D3 cell culture supernatant, 5 µL of conditioned medium were analyzed by SDS-8% PAGE. The transblotted membranes were then probed with a rabbit polyclonal anti-human fibronectin (dilution 1:1000 from Sigma). Anti-rabbit peroxidase-conjugated secondary antibody was used (dilution 1:2500, Jackson Immunoresearch laboratories) followed by chemiluminscent detection.

Statistical Analysis

Data are presented as medians (quartiles) for continuous variables and percentages for qualitative variables. We analysed data by either a Mann-Whitney U test or, in cases where more than one group is compared, by a Kruskal-Wallis test followed, if $P<0.05$, by a Mann-Whitney U test. Comparison of mortality between groups was performed using the Fisher exact test. A 2-tailed value of $P<0.05$ was considered significant. Data were analyzed using JMP 7.0.1.

Results

In Vivo Experiments

Baseline Characteristics

Physiological characteristics (body weight, body temperature, glycemia, blood pressure, and blood gases) did not differ across groups through the experiments.

Effect of Combination Treatment with tPA and HDL on Mortality, Infarct Volume, and Neurological Deficit To test whether HDL infusion may be effective in preventing deleterious effects of tPA injected at the reperfusion stage, tPA±HDL was administered 4 hours after stroke onset and compared with control groups (saline or HDL alone), in two models of stroke in rats. tPA increased infarct volume and mortality in both filament and embolic models as detailed in the FIG. 13. The mortality rate observed in the tPA-treated group was higher in fMCAO than in eMCAO group (86.05 versus 56.25%; P=0.0089). Additional treatment with HDL significantly decreased both infarct volume and mortality relative to tPA treatment alone in both models (FIG. 13). HDL treatment alone significantly reduced cerebral infarct volume compared with saline in both stroke models but only a trend for decreased mortality was observed. Combined treatment also improved the neurological outcome relative to tPA treatment alone in both models (fMCAO, p=0.009; eMCAO, p=0.01, data not shown).

Effects of HDL Treatment on Hemorrhagic Transformation and Cerebral Edema Induced by tPA.

Since the major complications associated with tPA treatment are hemorrhagic transformation and edema, we tested the effect of HDL in our models of stroke on these particular endpoints. Only the groups treated by tPA alone exhibited a high percentage of parenchymal hematoma (P) (fMCAO, 62.86%, eMCAO, 46.67%) which was strongly associated with mortality (P=0.022, FIG. 14). No significant difference was observed for the rate of petechial hemorrhage between groups. Interestingly, combination treatment of tPA with HDL dramatically decreased the incidence of parenchymal hematoma by more than 90% in both models compared to combined tPA and saline treatment (P<0.001), (FIG. 14).

Effects of Combined Treatment on Blood Brain Barrier Integrity

To assess the effect of combined treatment on BBB integrity, cerebral edema and IgG extravasation were evaluated as a surrogate marker of BBB disruption during acute stroke. Large edema surrounding ischemic cerebral vessels were observed only in tPA-treated group compared to HDL+tPA group. Increased IgG extravasation was shown in the ipsilateral ischemic versus contralateral hemisphere across the different groups. Combination treatment with tPA and HDL significantly reduced IgG extravasation relative to tPA alone (FIG. 15). We then performed immunostaining for collagen IV, a main component of the basal lamina of cerebral microvessels. Twenty-four hours after stroke, the number of collagen IV immunoreactive vessels in the infarcted area was decreased compared with contralateral hemisphere in the saline group and even more in tPA-treated group. Combined HDL and rtPA therapy was associated with a significant increase of collagen IV immunoreactive vessels relative to tPA alone, suggesting an improved BBB integrity (FIG. 16).

HDL Uptake by Cerebral Endothelial Cells In Vivo

In order to produce a significant effect on tPA-associated complications, we hypothesized that injected HDL should quickly reach the ischemic area and be taken up by cerebral endothelial cells. HDL were internalized as soon as one hour after injection and remain detectable within endothelial cells during 24 hours.

HDL Prevented tPA-Induced BBB Injury In Vitro

We hypothesized that the beneficial in vivo effects of HDL on complications associated with tPA treatment in vivo at the acute phase of stroke (hemorrhage, edema) may be due, at least in part, to the protection of the BBB. We thus assessed BBB integrity using an in vitro model subjected to oxygen glucose deprivation (OGD) in the presence of tPA±HDL. In our conditions (4 hours of stimulation), neither tPA nor OGD were sufficient to induce increased BBB permeability. VE-cadherin is a pivotal junctional protein involved in the maintenance of endothelial barrier restricted permeability. Immunofluorescent staining for VE-cadherin, performed on hCMEC/D3 cells 7 days post-confluence, showed that tPA induced a disorganization of intercellular junctions characterized by intracellular patches of VE-cadherin. Supplementation with HDL reduced, at least partially, this phenotype by maintaining the cell-cell junctions. Western Blot analysis for soluble fibronectin, a component of cerebral basal lamina, showed that tPA induced an important release of fibronectin/fragments in the corresponding supernatants. HDL only weakly limited this pericellular proteolytic process.

In Vitro and Ex Vivo Assessment of HDL on tPA Activity

Since HDL display anti-protease properties, we tested the hypothesis that HDL may inhibit tPA activity in vitro and ex vivo. Using a selective subtrate of tPA, we show that HDL did not modify tPA proteolytic activity, in vitro (FIG. 17A). These results were further supported ex vivo in plasma of rats that received i.v administration of tPA and HDL. The proteolytic activity of tPA from rat plasma was not affected by concomitant injection of HDL (FIG. 17B) suggesting that a combined treatment is possible without interference with tPA fibrinolytic action.

Conclusion tPA-treated groups had significantly higher mortality and rate of HT at 24 hours in both MCAO models. Combined treatment with HDL decreased tPA-induced intracerebral parenchymal hematoma and cerebral edema. This was consistent with an increased BBB integrity. Co-treatment with HDL also reduced significantly stroke-induced mortality and infarct size ($P<0.05$). In vitro, tPA-induced BBB disorganization was decreased by co-treatment with HDL.

The inventors thus showed that HDL injection decreased tPA-induced hemorrhagic transformation in rat models of MCAO. This indicates an HDL-dependent protective action on BBB integrity.

References

Throughout this application, various references describe the state of the art to which this invention pertains. The disclosures of these references are hereby incorporated by reference into the present disclosure.

The invention claimed is:

1. A method for protecting the blood brain barrier from the deleterious effect of an injection of tissue plasminogen activator, in a subject suffering from stroke and in need of treatment comprising administering by injection to said subject tissue plasminogen activator to said subject, and administering by injection to said subject an amount of HDL, wherein the amount of HDL is effective to protect the blood brain barrier and reduce the incidence of hemorrhage induced by tissue plasminogen activator, wherein the HDL is administered at the same time as the tissue plasminogen activator injection, or within 5 hours after administration the tissue plasminogen activator injection.

2. The method according to claim 1, wherein said HDL further comprises an additional agent selected from the group consisting of antiproteases, antioxidants, antimitotics, agents involved in the iron metabolism and anti-apoptotic agents.

3. The method according to claim 1, wherein said HDL is native or reconstituted.

4. The method according to claim 2, wherein said agent is an antiprotease selected from the group consisting of alpha-1 antitrypsin, elafin, protease-nexin 1, alpha-2-anti-plasmin, monocyte/neutrophil elastase inhibitor, inter-alpha-trypsin inhibitor, tissue-inhibitors of Matrix Metalloproteinases and alpha-1 antichymotrypsin.

5. The method according to claim 4, wherein the amount of antiprotease provides a molar ratio of antiprotease to apolipoprotein A-I that is associated with the amount of HDL of between 0.1 and 200.

6. The method according to claim 2, wherein said agent is an antioxidant selected from the group consisting of Paraoxonase 1,2,3, Catalase, Vitamin E, Omega-3 fatty acids, Butylated Hydroxytoluene, N-acetyl cystein, Polyphenols, Thioredoxins, and Estrogens.

7. The method according to claim 6, wherein the amount of antioxidant provides a molar ratio of antioxidant to apolipoprotein A-I of between 0.1 and 200.

8. The method according to claim 2, wherein said antimitotic is Siromilus.

9. The method according to claim 8, wherein the amount of antimitotic provides a molar ratio of antimitotic to apolipoprotein A-I of between 0.1 and 200.

10. The method according to claim 2, wherein said agent is an agent involved in iron metabolism selected from the group comprising transferrin, haptoglobin and hepcidin.

11. The method according to claim 10, wherein the amount of agent provides a molar ratio of agent involved in iron metabolism to apolipoprotein A-I of between 0.1 to 200.

12. The method according to claim 2, wherein said agent is an anti-apoptotic agent selected from the group comprising Sphingosine-1-phosphate, Paraoxonase 1 and 2, Catalase, Omega-3 fatty acids including DHA, Resolvin E1 and Clusterin.

13. The method according to claim 12, wherein the amount of anti-apoptotic agent provides a molar ratio of anti-apoptotic agent to apolipoprotein A-I of between 0.1 to 400.

* * * * *